(12) United States Patent
Piferi et al.

(10) Patent No.: US 8,195,272 B2
(45) Date of Patent: Jun. 5, 2012

(54) MRI-COMPATIBLE PATCHES AND METHODS FOR USING THE SAME

(75) Inventors: Peter Piferi, Orange, CA (US); Raffaele Mazzei, Encinitas, CA (US); Alex Diener, Seattle, WA (US); Brady Steele, Encinitas, CA (US)

(73) Assignee: MRI Interventions, Inc., Memphis, TN (US)

( * ) Notice: Subject to any disclaimer, the term of this patent is extended or adjusted under 35 U.S.C. 154(b) by 802 days.

(21) Appl. No.: 12/236,621

(22) Filed: Sep. 24, 2008

(65) Prior Publication Data

US 2009/0177077 A1    Jul. 9, 2009

Related U.S. Application Data

(60) Provisional application No. 60/974,821, filed on Sep. 24, 2007.

(51) Int. Cl.
*A61B 5/055* (2006.01)
*A61B 19/00* (2006.01)
*A61B 19/08* (2006.01)

(52) U.S. Cl. ........ 600/414; 600/411; 600/415; 600/410; 128/845; 128/846; 128/849; 378/162; 378/163; 378/164

(58) Field of Classification Search .......... 128/845, 128/846, 849; 378/162, 163, 164
See application file for complete search history.

(56) References Cited

U.S. PATENT DOCUMENTS

| | | | |
|---|---|---|---|
| 4,319,136 A | 3/1982 | Jinkins | |
| 4,386,602 A | 6/1983 | Sheldon et al. | |
| 4,838,265 A | 6/1989 | Cosman et al. | |
| 5,052,035 A | 9/1991 | Krupnick | |
| 5,125,888 A | 6/1992 | Howard et al. | |
| 5,154,723 A | 10/1992 | Kubota et al. | |
| 5,260,985 A | 11/1993 | Mosby | |
| 5,342,356 A | 8/1994 | Ellman et al. | |
| 5,427,099 A | 6/1995 | Adams | |
| 5,469,847 A | 11/1995 | Zinreich et al. | |

(Continued)

FOREIGN PATENT DOCUMENTS

DE    196 25 834 A1    1/1998

(Continued)

OTHER PUBLICATIONS

Martin et al., Placement of Deep Brain Stimulator Electrodes Using Real-Time High-Field Interventional Magnetic Resonance Imaging, Magnetic Resonance in Medicine, 2005, 54:1107-1114.

(Continued)

*Primary Examiner* — Long V. Le
*Assistant Examiner* — Farshad Negarestan
(74) *Attorney, Agent, or Firm* — Myers Bigel Sibley & Sajovec, PA

(57) ABSTRACT

An MRI-compatible patch for identifying a location includes a flexible base layer, a flexible substrate and at least one of MRI-visible fiducial element. The flexible base layer is mountable on and substantially conformable to a patient's body surface. The base layer has opposed upper and lower primary surfaces. The flexible substrate is releasably attached to the upper primary surface of the base layer and substantially conformable to the patient's body surface. The at least one MRI-visible fiducial element is defined by or secured to the flexible substrate. The patch may include a plurality of the MRI-visible fiducial elements arranged in a defined pattern.

29 Claims, 15 Drawing Sheets

U.S. PATENT DOCUMENTS

| | | | |
|---|---|---|---|
| 5,638,819 | A | 6/1997 | Manwaring et al. |
| 5,655,084 | A | 8/1997 | Pinsky et al. |
| 5,695,501 | A | 12/1997 | Carol et al. |
| 5,697,958 | A | 12/1997 | Paul et al. |
| 5,699,801 | A | 12/1997 | Atalar et al. |
| 5,707,335 | A | 1/1998 | Howard et al. |
| 5,728,079 | A | 3/1998 | Weber et al. |
| 5,743,899 | A | 4/1998 | Zinreich |
| 5,776,144 | A | 7/1998 | Leysieffer et al. |
| 5,779,694 | A | 7/1998 | Howard et al. |
| 5,928,145 | A | 7/1999 | Ocali et al. |
| 5,961,455 | A | 10/1999 | Daum et al. |
| 5,993,463 | A | 11/1999 | Truwit |
| 6,006,126 | A | 12/1999 | Cosman |
| 6,050,992 | A | 4/2000 | Nichols |
| 6,119,032 | A | 9/2000 | Martin et al. |
| 6,159,497 | A * | 12/2000 | LaPrade et al. ............... 424/448 |
| 6,167,292 | A | 12/2000 | Badano et al. |
| 6,167,311 | A | 12/2000 | Rezai |
| 6,195,577 | B1 | 2/2001 | Truwit et al. |
| 6,206,890 | B1 | 3/2001 | Truwit |
| 6,216,030 | B1 | 4/2001 | Howard et al. |
| 6,263,229 | B1 | 7/2001 | Atalar et al. |
| 6,267,769 | B1 | 7/2001 | Truwit |
| 6,267,770 | B1 | 7/2001 | Truwit |
| 6,273,896 | B1 | 8/2001 | Franck et al. |
| 6,282,437 | B1 | 8/2001 | Franck et al. |
| 6,284,971 | B1 | 9/2001 | Atalar et al. |
| 6,298,262 | B1 | 10/2001 | Franck et al. |
| 6,351,662 | B1 | 2/2002 | Franck et al. |
| 6,356,786 | B1 | 3/2002 | Rezai et al. |
| 6,368,329 | B1 | 4/2002 | Truwit |
| 6,405,079 | B1 | 6/2002 | Ansarinia |
| 6,419,680 | B1 | 7/2002 | Cosman et al. |
| 6,438,423 | B1 | 8/2002 | Rezai et al. |
| 6,526,318 | B1 | 2/2003 | Ansarinia |
| 6,529,765 | B1 | 3/2003 | Franck et al. |
| 6,539,263 | B1 | 3/2003 | Schiff et al. |
| 6,584,351 | B1 | 6/2003 | Ekwall |
| 6,606,513 | B2 | 8/2003 | Lardo et al. |
| 6,609,030 | B1 | 8/2003 | Rezai et al. |
| 6,628,980 | B2 | 9/2003 | Atalar et al. |
| 6,675,033 | B1 | 1/2004 | Lardo et al. |
| 6,701,176 | B1 | 3/2004 | Halperin et al. |
| 6,708,064 | B2 | 3/2004 | Rezai |
| 6,725,092 | B2 | 4/2004 | MacDonald et al. |
| 6,752,812 | B1 | 6/2004 | Truwit |
| 6,772,000 | B2 | 8/2004 | Talpade |
| 6,782,288 | B2 | 8/2004 | Truwit et al. |
| 6,904,307 | B2 | 6/2005 | Karmarkar et al. |
| 6,920,347 | B2 | 7/2005 | Simon et al. |
| 7,155,316 | B2 | 12/2006 | Sutherland et al. |
| 7,167,760 | B2 | 1/2007 | Dawant et al. |
| 7,217,276 | B2 | 5/2007 | Henderson et al. |
| 7,235,084 | B2 | 6/2007 | Skakoon et al. |
| 7,241,283 | B2 | 7/2007 | Putz |
| 2001/0004676 | A1 | 6/2001 | Ouchi |
| 2001/0014771 | A1 | 8/2001 | Truwit et al. |
| 2001/0053879 | A1 | 12/2001 | Mills et al. |
| 2002/0010479 | A1 | 1/2002 | Skakoon et al. |
| 2002/0019641 | A1 | 2/2002 | Truwit |
| 2002/0049451 | A1 | 4/2002 | Parmer et al. |
| 2002/0052610 | A1 | 5/2002 | Skakoon et al. |
| 2003/0028095 | A1 | 2/2003 | Tulley et al. |
| 2003/0050557 | A1 | 3/2003 | Susil et al. |
| 2003/0055436 | A1 | 3/2003 | Daum et al. |
| 2003/0120143 | A1 | 6/2003 | Franklin et al. |
| 2004/0046557 | A1 | 3/2004 | Karmarkar et al. |
| 2004/0064148 | A1 | 4/2004 | Daum et al. |
| 2004/0092810 | A1 | 5/2004 | Daum et al. |
| 2004/0167543 | A1 | 8/2004 | Mazzocchi et al. |
| 2004/0215279 | A1 | 10/2004 | Houben et al. |
| 2004/0228796 | A1 | 11/2004 | Talpade |
| 2004/0267284 | A1 | 12/2004 | Parmer et al. |
| 2005/0070781 | A1 | 3/2005 | Dawant et al. |
| 2005/0193609 | A1* | 9/2005 | Schwartz ........................ 40/638 |
| 2005/0222647 | A1 | 10/2005 | Wahlstrand et al. |
| 2006/0192319 | A1 | 8/2006 | Solar |
| 2006/0195119 | A1 | 8/2006 | Mazzocchi et al. |
| 2006/0195134 | A1* | 8/2006 | Crittenden .................... 606/192 |
| 2006/0229641 | A1 | 10/2006 | Gupta et al. |
| 2006/0241400 | A1 | 10/2006 | Bucholz |
| 2006/0252314 | A1 | 11/2006 | Atalar et al. |
| 2007/0106305 | A1 | 5/2007 | Kao et al. |
| 2007/0118049 | A1 | 5/2007 | Viola |
| 2008/0039709 | A1 | 2/2008 | Karmarkar |
| 2008/0306375 | A1 | 12/2008 | Sayler et al. |

FOREIGN PATENT DOCUMENTS

| | | |
|---|---|---|
| DE | 100 29 736 A1 | 3/2002 |
| DE | 100 29 737 A1 | 5/2003 |
| EP | 1 524 626 A | 4/2005 |
| WO | WO 98/52064 | 11/1998 |
| WO | WO 03/102614 | 12/2003 |
| WO | WO 2004/029782 | 4/2004 |
| WO | WO 2004/058086 | 6/2004 |
| WO | WO 2006/081409 | 8/2006 |
| WO | WO 2006/099475 A2 | 9/2006 |
| WO | WO 2007/064739 | 6/2007 |
| WO | WO 2007/106558 A2 | 9/2007 |

OTHER PUBLICATIONS

Lin et al., "A Wavelet-Based Approximation of Surface Coil Sensitivity Profiles for Correction of Image Intensity Inhomogeneity and Parallel Imaging Reconstruction," *Human Brain Mapping* 2003, 19(2):96-111.

Sauser, Brittany, A 3-D View of the Brain, http://www.technologyreview.com/Biotech/19140, Aug. 6, 2007, 3 Pages.

Singh et al., "Accurate Intensity Correction for Endorectal Surface Coil MR Imaging of the Prostate," IEEE Transactions on Nuclear Science, 1993, 40(4):1169-1173.

Jorgensen, Erik, Brain Image Analsis Team Joins SCI Institute, http://www.sci.utah.edu/stories/2007/Gerig_NeuroimageAnalysis.html, (2007), 3 Pages.

Baker et al., Neurostimulation systems: assessment of magnetic field interactions associated with 1.5- and 3-Tesla MR systems, J Magn Reson Imaging, 2005, 72-77, 21(1).

Bhidayasiri et al., Bilateral neurostimulation systems used for deep brain stimulation: in vitro study of MRI-related heating at 1.5 T and implications for clinical imaging of the brain, Magn Reson Imaging, 2005, 549-555, 23(4).

Buchli et al., Increased RF power absorption in MR imaging due to RF coupling between body coil and surface coil, Magn Reson Med, 1989, 105-112, 9(1).

Dorward et al., Accuracy of true frameless stereotaxy: in vivo measurement and laboratory phantom studies, J. Neurosurg., 1999, 90:160-168.

Francel, Nexframe System, Bilateral Activa Lead Delivery to STN Using Nexframe, Oklahoma University Presbyterian Hospital, Image-Guided Neurolgics.

Grimson et al., An automatic registration method for frameless stereotaxy, image guided surgery, and visualization, IEEE Tran on Medical Imaging, Apr. 1996, 129-140.

Hall et al., Brian biopsy sampling by using prospective stereotaxis and a trajectory guide, J. Neurosurg., 2001, 94:67-71.

Liu et al., Remotely-Controlled Approach for Stereotactic Neurobiopsy, Computer Aided Surgery, 2002, 7:237-247.

Smith et al., The Neurostation—A Highly Accurate, Minimally Invasive Solution to Frameless Stereotactic Neurosurgery, Computerized Medical Imaging and Graphics, 1994, 247-256, 18(4).

STarFix™—Dr. Joel Franck and FHC engineer Ron Franklin—creators, www.tgt.vanderbilt.edu/reu2/REU2002/chris.ppt.

Tear Away Introducer Sets (INTRADYN), B. Braun Medical, Inc. http://www.bbraunusa.com.

Truwit et al., Prospective Stereotaxy: A Novel Method of Trajectory Alignment Using Real-Time Image Guidance, J. Magn. Reson. Imag., 2001, 13:452-457.

Willems et al., Frameless Stereotaxy, VHL Family Alliance, http://www.vhl.org/newsletter/vhl2000/00aefrst.htm.

Wirtz et al., Image-Guided Neurosurgery with Intraoperative MRI: Update of Frameless Stereotaxy and Radicality Control, Sterotact Funct Neurosurg 1997, 68:39-43.

Yoda, Decoupling technique for transmit coils in NMR spectroscopy and imaging, NMR Biomed, 1990, 27-30, 3(1).

Invitation to Pay Additional Fees and, Where Applicable, Protest Fee (4 pages) corresponding to International Application No. PCT/US2008/011078; Mailing Date: Jan. 14, 2009.

Martin et al., "Placement of Deep Brain Stimulator Electrodes Using Real-Time High-Field Interventional Magnetic Resonance Imaging," *Magnetic Resonance in Medicine*, 54:1107-1114 (2005).

* cited by examiner

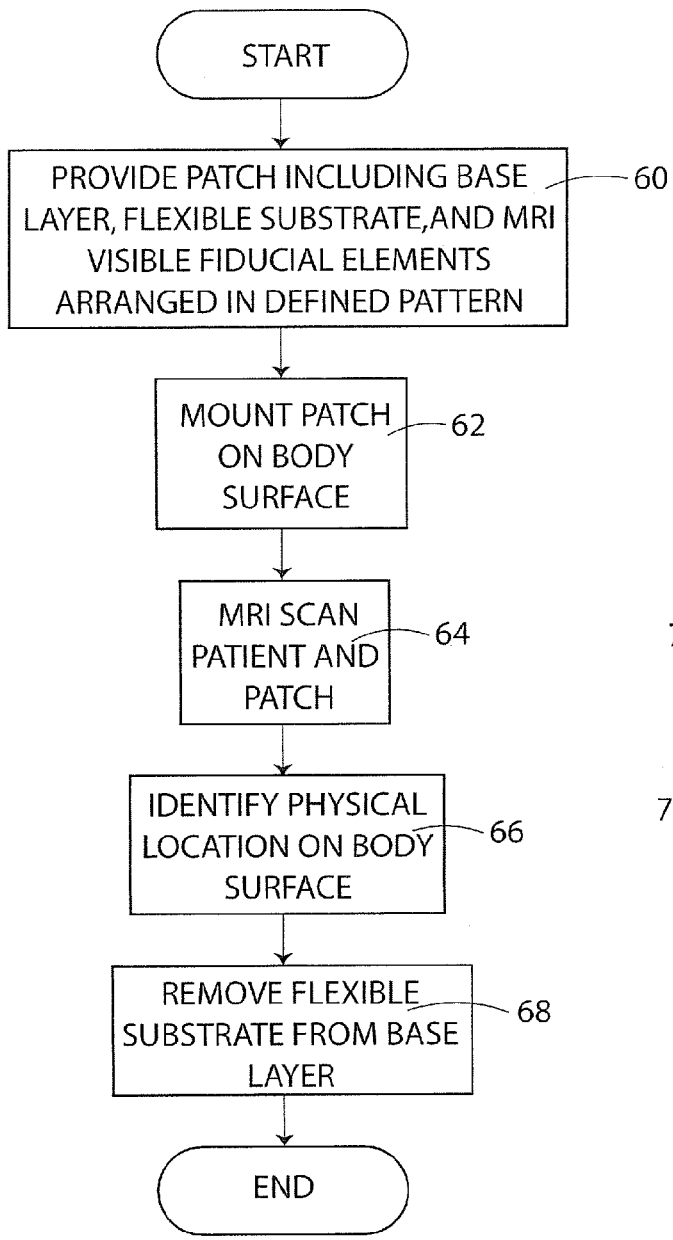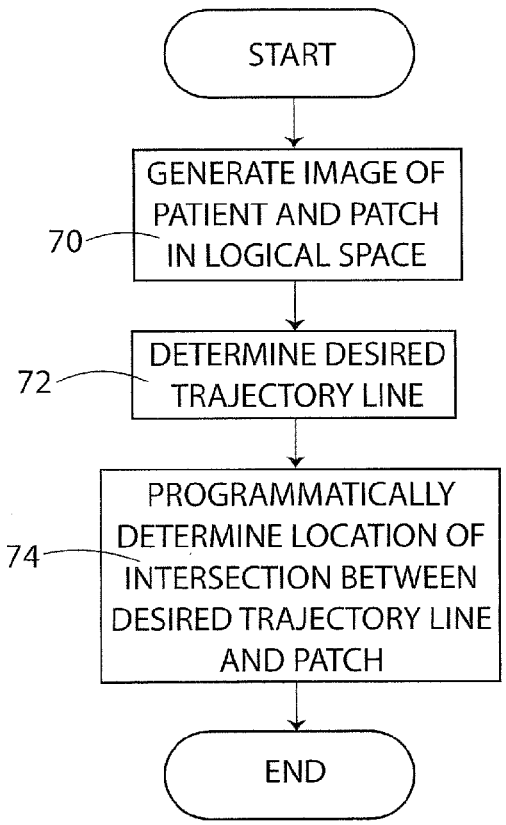

MRI-COMPATIBLE PATCHES AND METHODS FOR USING THE SAME

RELATED APPLICATION(S)

This application claims the benefit of and priority to U.S. Provisional Patent Application No. 60/974,821, filed Sep. 24, 2007, the disclosure of which is incorporated herein by reference as if set forth in its entirety.

FIELD OF THE INVENTION

The present invention relates generally to medical systems and methods and, more particularly, to in vivo medical systems and methods.

BACKGROUND OF THE INVENTION

Deep Brain Stimulation (DBS) is becoming an acceptable therapeutic modality in neurosurgical treatment of patients suffering from chronic pain, Parkinson's disease or seizure, and other medical conditions. Other electro-stimulation therapies have also been carried out or proposed using internal stimulation of the sympathetic nerve chain and/or spinal cord, etc.

One example of a prior art DBS system is the Activa® system from Medtronic, Inc. The Activa® system includes an implantable pulse generator stimulator that is positioned in the chest cavity of the patient and a lead with axially spaced apart electrodes that is implanted with the electrodes disposed in neural tissue. The lead is tunneled subsurface from the brain to the chest cavity connecting the electrodes with the pulse generator. These leads can have multiple exposed electrodes at the distal end that are connected to conductors which run along the length of the lead and connect to the pulse generator placed in the chest cavity.

It is believed that the clinical outcome of certain medical procedures, particularly those using DBS, may depend on the precise location of the electrodes that are in contact with the tissue of interest. For example, to treat Parkinson's tremor, presently the DBS probes are placed in neural tissue with the electrodes transmitting a signal to the thalamus region of the brain. DBS stimulation leads are conventionally implanted during a stereotactic surgery, based on pre-operative MRI and CT images. These procedures can be long in duration and may have reduced efficacy as it has been reported that, in about 30% of the patients implanted with these devices, the clinical efficacy of the device/procedure is less than optimum. Notwithstanding the above, there remains a need for alternative MRI-guided interventional tools for DBS, as well as for other interventional medical procedures.

SUMMARY OF THE INVENTION

According to embodiments of the present invention, an MRI-compatible patch for identifying a location includes a flexible base layer, a flexible substrate and at least one MRI-visible fiducial element. The flexible base layer is mountable on and substantially conformable to a patient's body surface. The base layer has opposed upper and lower primary surfaces. The flexible substrate is releasably attached to the upper primary surface of the base layer and substantially conformable to the patient's body surface. The at least one MRI-visible fiducial element is defined by or secured to the flexible substrate. The MRI-visible fiducial elements are arranged in a defined pattern.

According to some embodiments, the patch includes an adhesive to releasably attach the flexible substrate to the base layer.

The patch may include an adhesive disposed on the lower primary surface of the base layer to attach the base layer to the body surface.

The patch may include indicia on the base layer corresponding to the MRI-visible fiducial elements on the flexible substrate. The patch may include second indicia on the flexible substrate corresponding to the indicia on the base layer.

In some embodiments, the patch includes a plurality of the MRI-visible fiducial elements. The fiducial elements may be arranged in a defined pattern. Indicia may be provided on the base layer corresponding to the MRI-visible fiducial elements on the flexible substrate, wherein the indicia has a second prescribed pattern having a higher resolution than the defined pattern of the MRI-visible fiducial elements on the flexible substrate. In some embodiments, the defined pattern includes a grid pattern defining a coordinate system. The patch may include codified indicia representing the coordinate system.

The flexible substrate can include a pull tab to facilitate removal of the flexible substrate from the base layer.

In some embodiments, the base layer is frangible to permit selective access to the body surface when the base layer is mounted thereon and the flexible substrate has been at least partially removed.

According to some embodiments, the patch includes at least one MRI-visible reference indicator to indicate an orientation of the patch.

In some embodiments, at least one of the MRI-visible fiducial elements has a first MRI-visible geometric shape, and at least one of the MRI-visible fiducial elements has a second MRI-visible geometric shape different from the first MRI-visible geometric shape.

According to some embodiments, at least some of the MRI-visible fiducial elements include a pocket containing MRI-visible material. The MRI-visible material may include an MRI-visible liquid.

At least some of the MRI-visible fiducial elements may be selectively discretely removable from the flexible substrate to permit access to the body surface.

According to some embodiments, the patch includes perforations defined in the flexible substrate to thereby enhance conformity of the flexible substrate to the body surface.

The flexible substrate can be formed of a stretchable material to allow the flexible substrate to conform to a head body surface.

According to some embodiments, the flexible substrate has a thickness in the range of from about 0.001 to 0.100 inches.

According to some embodiments, the flexible substrate is a substrate material selected from the group consisting of polyvinyl, PET, silicone, polyethylene, polyurethane, and polyamide.

According to some embodiments, the patch further includes: a plurality of MRI-visible fiducial elements defined by or secured to the flexible substrate, wherein the fiducial elements are arranged in a defined pattern; an adhesive disposed on the lower primary surface of the base layer to attach the base layer to the body surface; a release liner backing and releasably secured to the adhesive; and indicia on the base layer corresponding to the MRI-visible fiducial elements on the flexible substrate; and at least one MRI-visible reference indicator to indicate an orientation of the patch; wherein at least some of the MRI-visible fiducial elements include a pocket containing MRI-visible liquid, and wherein the defined pattern includes a grid pattern defining a coordinate system.

According to embodiments of the present invention, a method for identifying a physical location on a body surface of a patient includes providing a patch including: a flexible base layer that is mountable on and substantially conformable to a patient's body surface, the base layer having opposed upper and lower primary surfaces; a flexible substrate that is releasably attached to the upper primary surface of the base layer and substantially conformable to the patient's body surface; and at least one MRI-visible fiducial element defined by or secured to the flexible substrate. The method further includes: securing the base layer to the body surface to mount the patch on the body surface such that the flexible substrate conforms to the body surface; MRI scanning the patient with the patch on the body surface to generate corresponding image data; identifying a physical location on the body surface using the image data; and removing the flexible substrate from the base layer.

According to some embodiments, the patch includes a plurality of the MRI-visible fiducial elements. In some embodiments, the fiducial elements are arranged in a defined pattern.

According to embodiments of the present invention, a method for identifying a physical location on a body surface of a patient residing in physical space includes providing a patch residing in physical space and including: a flexible substrate that is mountable on and substantially conformable to the body surface; and at least one MRI-visible fiducial element defined by or secured to the flexible substrate. The method further includes: mounting the patch on the body surface such that the flexible substrate conforms to the body surface; MRI scanning the patient with the patch on the body surface to generate corresponding image data; and identifying a physical location on the body surface using the image data, including: generating an image of the patient in a logical space; determining in the logical space a desired entry location on the body surface for insertion of instrumentation into the patient; and programmatically determining a physical location on the patch corresponding to the desired entry location.

In some embodiments, determining in the logical space the desired entry location includes determining a desired trajectory line, and determining the physical location on the patch corresponding to the desired entry location includes determining a location of intersection between the desired trajectory line and the patch. The method may include programmatically determining in the logical space the desired entry location and the desired trajectory line. The method can include displaying the desired entry location and the desired trajectory line on a display device to an operator.

According to some embodiments, the patch includes a plurality of the MRI-visible fiducial elements. In some embodiments, the fiducial elements are arranged in a defined pattern. According to some embodiments, the method includes displaying the image of the patient and a graphical overlay on a display to an operator. The graphical overlay indicates at least a portion of the defined pattern of the MRI-visible fiducial elements.

The method may further include marking the body surface at a location corresponding to the physical location on the patch.

According to some embodiments, the body surface is on the patient's head and the method includes forming a burr hole in the patient's skull proximate the physical location.

The mounting step may comprise releasably attaching the flexible substrate to the body surface prior to the step of MRI scanning the patient with the patch on the body surface. According to some embodiments, the patch includes a flexible base layer having opposed upper and lower primary surfaces, wherein the flexible substrate is releasably attached to the upper primary surface of the base layer, and the method includes: securing the base layer to the body surface prior to the step of MRI scanning the patient with the patch on the body surface; and removing the flexible substrate from the base layer after the step of MRI scanning the patient with the patch on the body surface.

The method may include removing at least one of the fiducial elements from the flexible substrate after the step of MRI scanning the patient with the patch on the body surface to permit access to the body surface.

In some embodiments, at least some of the MRI-visible fiducial elements include a pocket containing MRI-visible material.

In some embodiments, the method includes: mounting a plurality of the patches on the body surface in close proximity to one another; and thereafter MRI scanning the patient with the plurality of patches on the body surface to generate corresponding image data.

According to some embodiments, MRI scanning the patient with the patch on the body surface includes MRI scanning an MRI-visible reference indicator on the patch to generate corresponding reference image data. The method further includes programmatically determining an orientation of the patch using the reference image data.

According to embodiments of the present invention, a computer program product for identifying a physical location on a body surface of a patient using a patch mounted on the body surface and including at least one MRI-visible fiducial element includes a computer readable medium having computer usable program code embodied therein, the computer readable program code comprising: computer readable program code configured to generate an image of the patient and the patch in a logical space, the image corresponding to an MRI scan of the patient with the patch on the body surface; computer readable program code configured to determine in the logical space a desired trajectory line for insertion of instrumentation into the patient; and computer usable program code configured to programmatically determine a location of intersection between the desired trajectory line and the patch.

According to embodiments of the present invention, a system for designating a physical location on a body surface of a patient includes a patch and a controller. The patch includes: a flexible substrate that is mountable on and conformable to the body surface; and at least one MRI-visible fiducial element defined by or secured to the flexible substrate. The controller is adapted to communicate with an MRI scanner that is operable to scan the patient with the patch on the body surface and to generate corresponding image data. The controller processes the image data from the MRI scanner to programmatically identify a physical location on the body surface.

In some embodiments, the controller is operable to display correlated representations of the at least fiducial element and the patient.

According to embodiments of the present invention, a medical (surgical) kit for designating a physical location on a head of a patient includes a patch and a head marking tool. The patch includes a flexible base layer, a flexible substrate and at least one MRI-visible fiducial element. The flexible base layer is mountable on and substantially conformable to a patient's body surface. The base layer has opposed upper and lower primary surfaces. The flexible substrate is releasably attached to the upper primary surface of the base layer and substantially conformable to the patient's body surface. The MRI-visible fiducial element is defined by or secured to the flexible substrate. The head marking tool is configured to mark the head of the patient.

In some embodiments, the head marking tool is configured to mark a skull of the patent.

According to embodiments of the present invention, an MRI-compatible patch for identifying a location includes a flexible substrate that is mountable on and substantially conformable to a patient's body surface. A plurality of MRI-visible fiducial elements are defined by or secured to the flexible substrate. The MRI-visible fiducial elements are arranged in a defined pattern. The plurality of MRI-visible fiducial elements include at least one MRI-visible reference indicator to indicate an orientation of the patch.

According to embodiments of the present invention, a method for identifying a physical location on a body surface of a patient residing in physical space includes providing a patch residing in physical space and including: a flexible substrate that is mountable on and substantially conformable to the body surface; and at least one MRI-visible fiducial element defined by or secured to the flexible substrate. The method further includes: mounting the patch on the body surface such that the flexible substrate conforms to the body surface; MRI scanning the patient with the patch on the body surface to generate corresponding image data; generating an image of the patient in a logical space; and programmatically determining an orientation of the patch in the logical space using the image data.

In some embodiments, the patch includes an MRI-visible reference indicator and programmatically determining the orientation of the patch in the logical space using the image data includes programmatically determining the orientation of the patch in the logical space using image data corresponding to the MRI-visible reference indicator.

Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIGS. 1 and 2 are flowcharts representing methods according to embodiments of the present invention.

DETAILED DESCRIPTION OF EMBODIMENTS OF THE INVENTION

Figure 3:
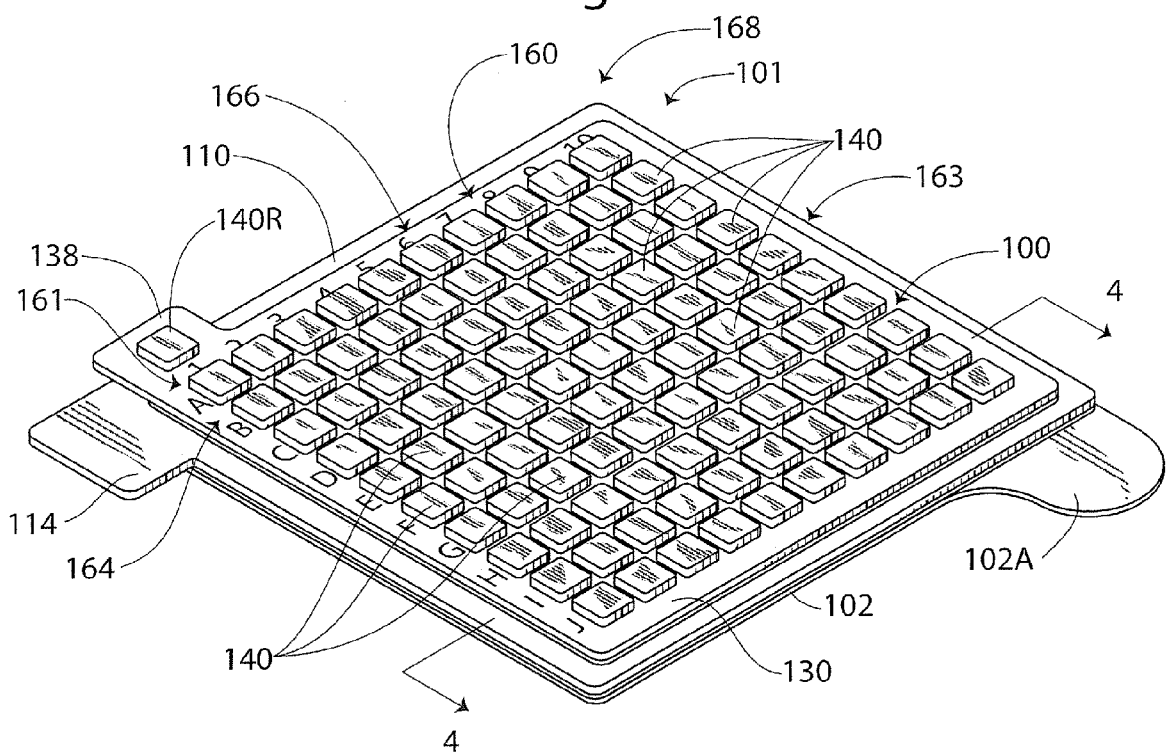
FIG. 3 is a top perspective view of an exemplary patch assembly according to embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Exemplary embodiments are described below with reference to block diagrams and/or flowchart illustrations of methods, apparatus (systems and/or devices) and/or computer program products. It is understood that a block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means (functionality) and/or structure for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the functions/acts specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, exemplary embodiments may be implemented in hardware and/or in software (including firmware, resident software, micro-code, etc.). Furthermore, exemplary embodiments may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of data processing systems discussed herein may be written in a high-level programming language, such as Java, AJAX (Asynchronous JavaScript), C, and/or C++, for development convenience. In addition, computer program code for carrying out operations of exemplary embodiments may also be written in other programming languages, such as, but not limited to, interpreted languages. Some modules or routines may be written in assembly language or even micro-code to enhance performance and/or memory usage. However, embodiments are not limited to a particular programming language. It will be further appreciated that the functionality of any or all of the program modules may also be implemented using discrete hardware components, one or more application specific integrated circuits (ASICs), or a programmed digital signal processor or microcontroller.

The flowcharts and block diagrams of certain of the figures herein illustrate exemplary architecture, functionality, and operation of possible implementations of embodiments of the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially.

The term "MRI-visible" means that a device or feature thereof is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled cavities.

The term "MRI-compatible" means that a device is safe for use in an MRI environment and/or can operate as intended in an MRI environment, and, as such, if residing within the high-field strength region of the magnetic field, is typically made of a non-ferromagnetic MRI-compatible material(s) suitable to reside and/or operate in a high magnetic field environment.

The term "programmatically" refers to operations directed and/or primarily carried out electronically by computer program modules, code and instructions.

The term "fiducial marker" refers to a marker that can be identified visually and/or using electronic image recognition, electronic interrogation of MRI image data, or three-dimensional electrical signals to define a position and/or find the feature or component in 3-D space.

Patches in accordance with embodiments of the present invention can be configured to identify or designate a location on a body. The location may be identified in order to determine a desired position, orientation or operation of a guide apparatus. The guide apparatus may be used to guide and/or place diagnostic or interventional devices and/or therapies to any desired internal region of the body or object using MRI and/or in an MRI scanner or MRI interventional suite. The object can be any object, and may be particularly suitable for animal and/or human subjects. In some embodiments, the guide apparatus is used to place implantable DBS leads for brain stimulation, typically deep brain stimulation. In some embodiments, the guide apparatus can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors. Some embodiments can be used for RF ablation, laser ablation, cryogenic ablation, etc. In some embodiments, the interventional tools can be configured to facilitate high resolution imaging via intrabody imaging coils (receive antennas), and/or the interventional tools can be configured to stimulate local tissue, which can facilitate confirmation of proper location by generating a physiologic feedback (observed physical reaction or via fMRI).

In some embodiments, the patch is used to identify a location on the body for delivering bions, stem cells or other target cells to site-specific regions in the body, such as neurological target and the like. In some embodiments, the patch is used to identify a location on the body for introducing stem cells and/or other cardio-rebuilding cells or products into cardiac tissue, such as a heart wall via a minimally invasive MRI-guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

Generally stated, some embodiments of the invention are directed to MRI interventional procedures including locally placing interventional tools or therapies in vivo to site-specific regions using an MRI system. The interventional tools can be used to define an MRI-guided trajectory or access path to an in vivo treatment site.

In some embodiments, MRI can be used to visualize (and/or locate) a therapeutic region of interest inside the brain or other body locations, to visualize an MRI-visible patch according to embodiments of the present invention, and to visualize (and/or locate) an interventional tool or tools that will be used to deliver therapy and/or to place a chronically implanted device that will deliver one or more therapies. Then, using the three-dimensional data produced by the MRI system regarding the location of the therapeutic region of interest and the location of the interventional tool, the system and/or physician can make positional adjustments to the interventional tool so as to align the trajectory of the interventional tool, so that when inserted into the body, the interventional tool will intersect with the therapeutic region of interest. With the interventional tool now aligned with the therapeutic region of interest, an interventional probe can be advanced, such as through an open lumen inside of the interventional tool, so that the interventional probe follows the trajectory of the interventional tool and proceeds to the therapeutic region of interest.

According to some methods of the present invention and with reference to FIG. 1, a method is provided for identifying a physical location on a body surface (e.g., the scalp) of a patient. A patch is provided including a flexible base layer that is mountable on and substantially conformable to the body surface and has opposed upper and lower primary surfaces, a flexible substrate that is releasably attached to the upper primary surface of the base layer and substantially conformable to the body surface, and a plurality of MRI-visible fiducial elements defined by or secured to the flexible substrate (Block 60). The MRI-visible fiducial elements are arranged in a defined pattern. The patch is mounted on the body surface such that the flexible substrate conforms to the body surface (Block 62). The patient is MRI scanned with the patch on the body surface to generate corresponding image data (Block 64). A physical location on the body surface is identified using the image data (Block 66). The flexible substrate is removed from the base layer (Block 68). Some embodiments of the present invention include a computer program product comprising computer usable program code embodied in a computer usable medium and configured to programmatically execute the step of identifying the physical location on the body surface using the image data.

According to some embodiments of the present invention and with reference to FIG. 2, a method is provided for identifying a physical location on a body surface of a patient using a patch mounted on the body surface. The patch includes a plurality of MRI-visible fiducial elements arranged in a defined pattern. An image of the patient and the patch in a logical space is generated (Block 70). The image corresponds to an MRI scan of the patient with the patch on the body surface. A desired trajectory line for insertion of instrumentation into the patient is determined in the logical space (Block 72). A location of intersection between the desired trajectory line and the patch is programmatically determined (Block 74). In some embodiments, the location of intersection is visually displayed. Some embodiments of the present invention include a computer program product comprising computer usable program code embodied in a computer usable medium and configured to programmatically determine the location of intersection between the desired trajectory line and the patch.

With reference to FIGS. 1-5, an integral patch assembly 101 according to embodiments of the present invention is shown therein. The patch assembly 101 includes a patch 100 and a release liner 102. The patch 100 includes a base substrate or layer 110, a primary or base adhesive 120, an MRI-visible or top substrate or layer 130, and a secondary or top adhesive 122.

Figure 4:
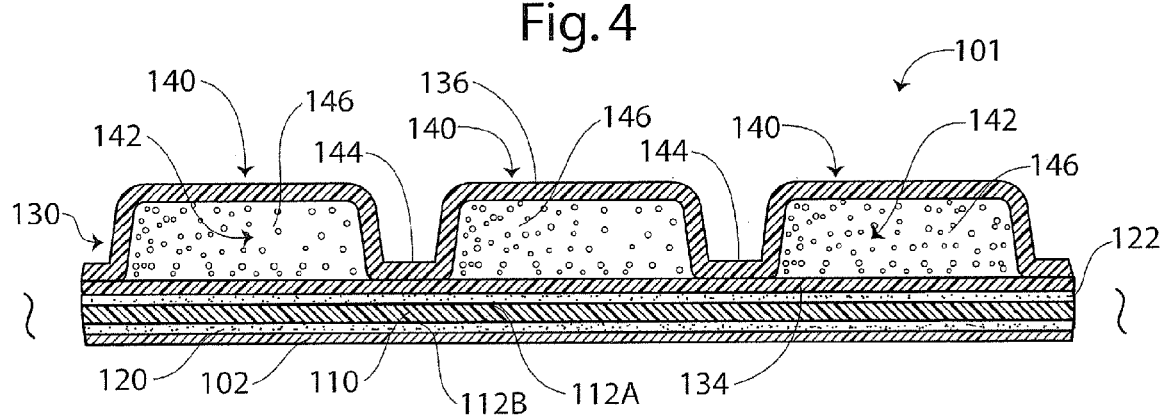
FIG. 4 is an enlarged, fragmentary, cross-sectional view of the patch assembly of FIG. 3 taken along the line 4-4 of FIG. 3.
Figure 5:
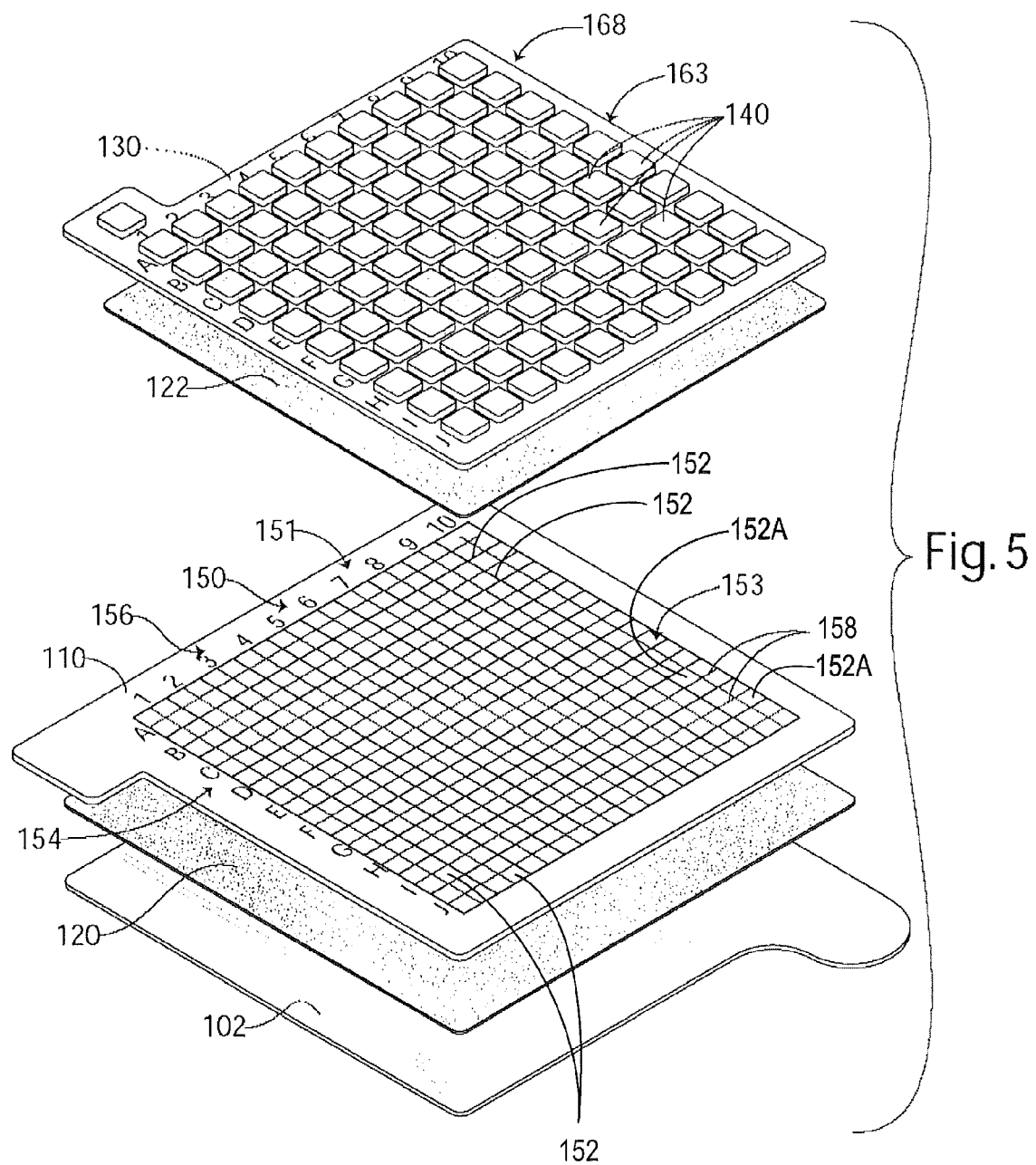
FIG. 5 is an exploded, top perspective view of the patch assembly of FIG. 3.

With reference to FIGS. 4 and 5, the base layer 110 has opposed upper and lower primary surfaces 112A, 112B. The base adhesive 120 coats the lower primary surface 112B. The release liner 102 is releasably adhered to the base layer 110 by the base adhesive 120, which remains with the base layer 110 when the release liner 102 is removed. The release line 102 may include a pull tab 102A. Optionally, the base layer 110 may include a pull tab 114 free of the adhesive 120.

The base layer 110 is formed of a flexible material. According to some embodiments, the base layer 110 is formed of a biocompatible polymeric material suitable for surgical use in MRI systems. Suitable polymeric materials may include polyvinyl, PET, silicone, polyethylene, polyurethane, and/or polyamide.

According to some embodiments, the base layer 110 has a thickness in the range of from about 0.001 to 0.100 inches. According to some embodiments, the base layer 110 has a total area in the range of from about 1 to 900 cm².

According to some embodiments, the base adhesive 120 is a biocompatible adhesive that has adhesive properties that ensure a secure, but releasable, bond with human skin and/or an incise drape.

With reference to FIGS. 3 and 4, the top layer 130 has an integral, bilayer construction including an inner layer 134 and an outer layer 136. However, other constructions in accordance with aspects of the invention are contemplated, as well. The top layer 130 has a lower surface that is coated with the top adhesive 122. The top layer 130 includes a pull tab 138 extending beyond an edge thereof. A portion or all of the pull tab 138 may be free of the adhesive 122.

The outer layer 136 is attached to the inner layer 134 at seams 144 (FIG. 4) to form a plurality of discrete pockets or cavities 142 (FIG. 4) between the seams 144 and the layers 134, 136. The layers 134, 136 may be attached via any suitable means such as bonded by adhesive, heat bonding or any other suitable technique. Each pocket 142 is filled with a mass 146 (FIG. 4) of an MRI-visible material 146 to form a respective MRI-visible fiducial element, bubble or tab 140. The plurality of tabs 140 can be arranged in a predefined array 168 and include a reference tab 140R (FIG. 3) positioned or shaped to be readily discerned with respect to the other tabs. While MRI-visible tabs 140, 140R are illustrated and described, other types and construction of MRI-visible fiducial elements may be employed in accordance with further embodiments. For example, the reference tab 140R may be replaced or supplemented with an MRI-visible coating.

The layers 134, 136 are formed of a flexible material. According to some embodiments, the layers 134, 136 are formed of a polymeric material. Suitable polymeric materials may include polyvinyl, PET, silicone, polyethylene, polyurethane, and/or polyamide.

The MRI-visible material 146 may be any suitable material. According to some embodiments, the MRI-visible material 146 is a liquid. According to some embodiments, the MRI-visible material 146 includes sterile saline or water (e.g., deionized water), with or without vitamin E and/or Gadolidium.

According to some embodiments, each pocket 142 has a volume in the range of about 50 to 500 microliters. According to some embodiments, each pocket 142 has a nominal height in the range of from about 0.010 to 1 inch. According to some embodiments, each pocket 142 has an area in the range of from about 4 mm² to 4 cm².

According to some embodiments, the top layer 130 has a nominal thickness in the range of from about 0.001 to 0.1 inch. According to some embodiments, the top layer 130 has a total area in the range of from about 1 to 900 cm².

According to some embodiments, the top adhesive 122 is a biocompatible adhesive that has adhesive properties that ensure a secure, but releasable bond with base layer 110.

The MRI-visible tabs 140 can be arranged in a defined pattern 163 (FIG. 3). According to some embodiments and as illustrated, the defined pattern 163 is a grid pattern, wherein the grid is demarcated by the voids between the masses 146 of MRI-visible material (generally, the seams 144). The defined pattern 163 defines a coordinate system 161. The coordinate system 161 may be codified in any suitable manner. For example, as illustrated, letter indicia 164 (i.e., "A" to "J") are provided to designate respective rows of the tabs 140 and number indicia 166 (i.e., "1" to "10") are provided to designate respective columns of the tabs 140 in the coordinate system 161. However, other markings or indicators as well as other languages may be used.

According to some embodiments, the predefined tab array 168 includes a grouping of at least five-by-five tabs 140.

The reference tab 140R of the tab array 140 is positioned to indicate an orientation of the top layer 130. According to some embodiments, the reference tab 140R (or other reference MRI-visible fiducial element) has a shape that is discernibly dissimilar from the other tabs 140 in an MR image. In this case, the reference tab 140R may not be positioned to indicate the orientation, but rather the orientation may be indicated by the orientation of the reference tab 140R.

Base indicia 150 (FIG. 5) can be provided on the base layer 110 and define a prescribed pattern and a corresponding coordinate system 151 that in turn corresponds to the coordinate system 161. The base indicia may be provided on the base layer 110 by etching, printing, molding, embossing, stamping, pressing or any other suitable technique. According to some embodiments and as illustrated, the base indicia 150 include grid lines 152 defining a matrix or grid 153 of sectors 152A. Letter indicia 154 (i.e., "A" to "J") are provided to designate respective rows of the sectors 152A and number indicia 156 (i.e., "1" to "10") are provided to designate respective columns of the sectors 152A. Four subsector marks 158 (as shown, cross-hairs or grid lines) are provided in each sector 152A to designate quadrants of the sector 152A.

Greater on lesser numbers of rows, columns, markers, and subsectors may be provide.

The indicia 154, 156 serve as codified indicia representing or corresponding to the coordinate system 161 of the tab array 168. Each of the sectors 152A may be sized and positioned to substantially coextensively align with a respective matched or overlying one of the tabs 140. The prescribed pattern of the base indicia 150 has higher resolution than the defined pattern of the array 168 of MRI-visible tabs 140 because the base indicia 150 further include the subsector marks 158 in each sector 152A.

Operations associated with an exemplary surgical procedure using the patch assembly 101, according to some embodiments of the present invention, will now be described with further reference to FIGS. 6-15. These operations relate to deep brain stimulation procedures. Embodiments of the present invention are not limited to use with deep brain stimulation procedures, however, and may be suitable for other surgical uses including robotic or other type of intrabody surgeries.

Figure 7:
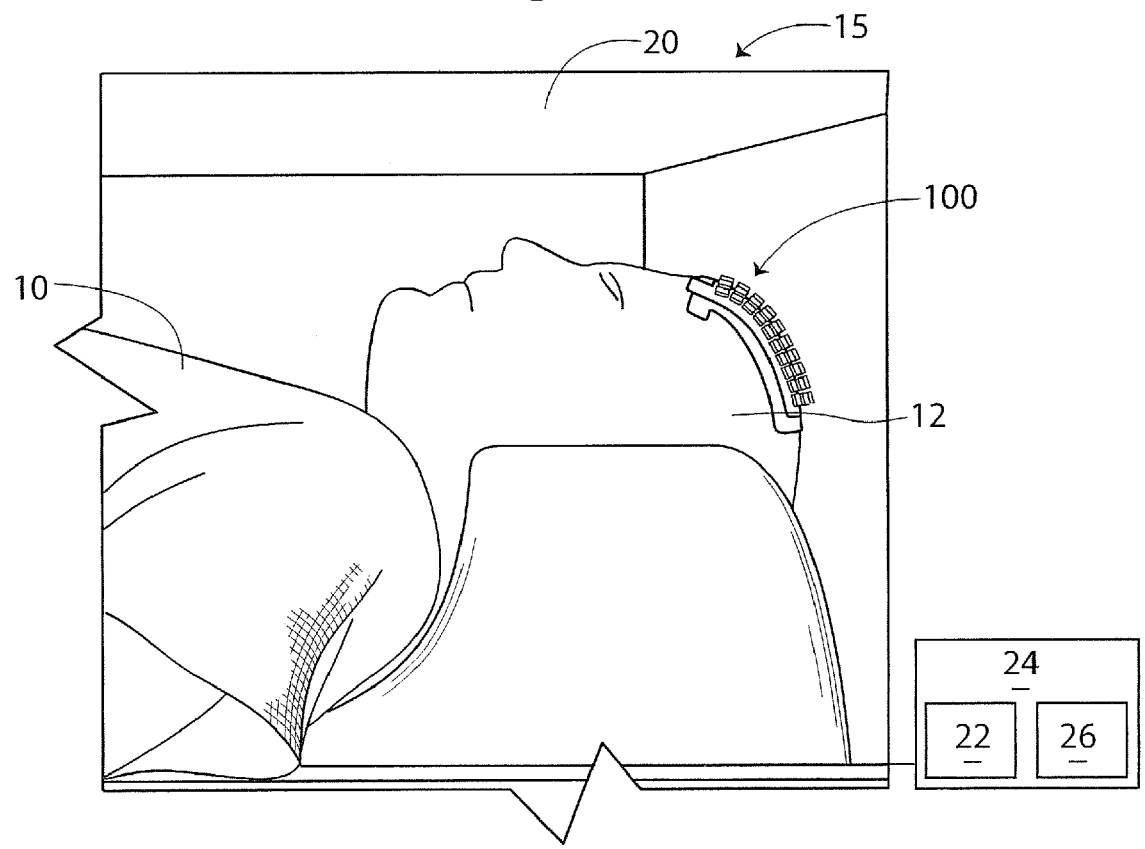
Figure 15:
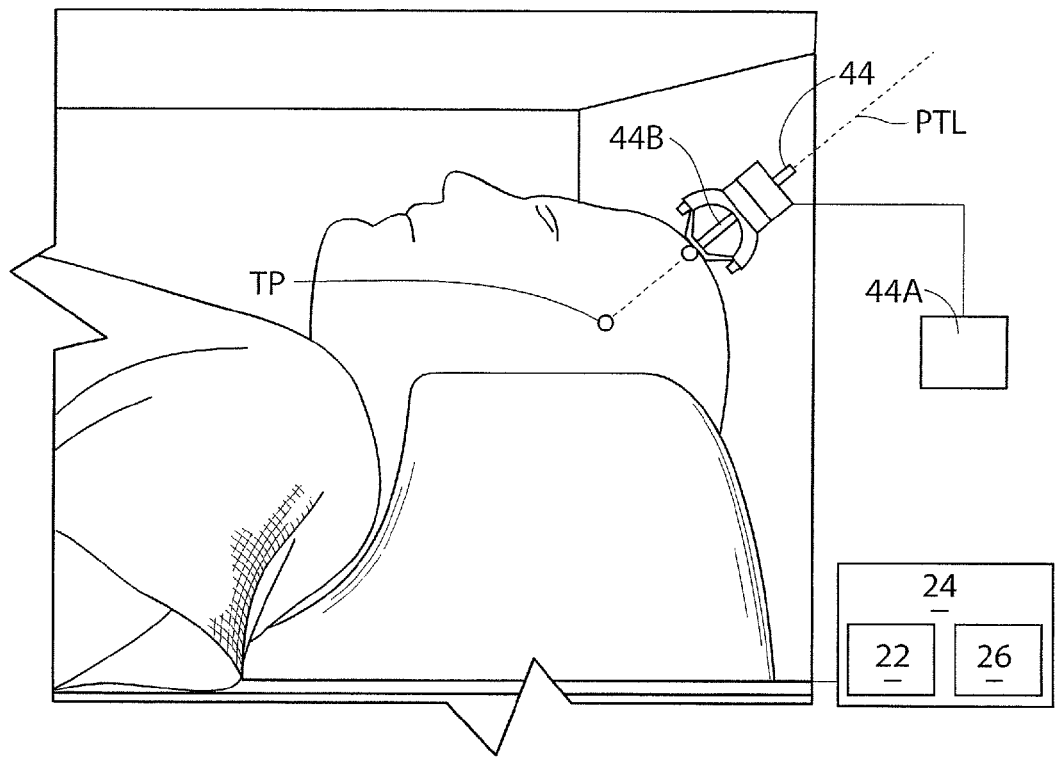

With reference to FIG. 7, the operations may be executed on a head 12 of a patient 10 using a patch assembly 101 as described above and an interventional system 15. The system 15 includes or is in communication with an MRI scanner 20, a display 22, an electronic controller 24, a user interface 26, a trajectory guide apparatus 44 (FIG. 15), and a device controller 44A (FIG. 15). The controller 24 may include a trajectory guide module 24B and a patch recognition module 24A (which may be software or firmware modules, for example).

The controller 24 may be any suitable computer(s) or the like adapted to carry out the functions described herein. The user interface 26 may include a man-machine interface to enable an operator to access and control operations of the system 15. The controller 24 can be operably connected to each of the display 22 and the MRI scanner 20.

Figure 6:
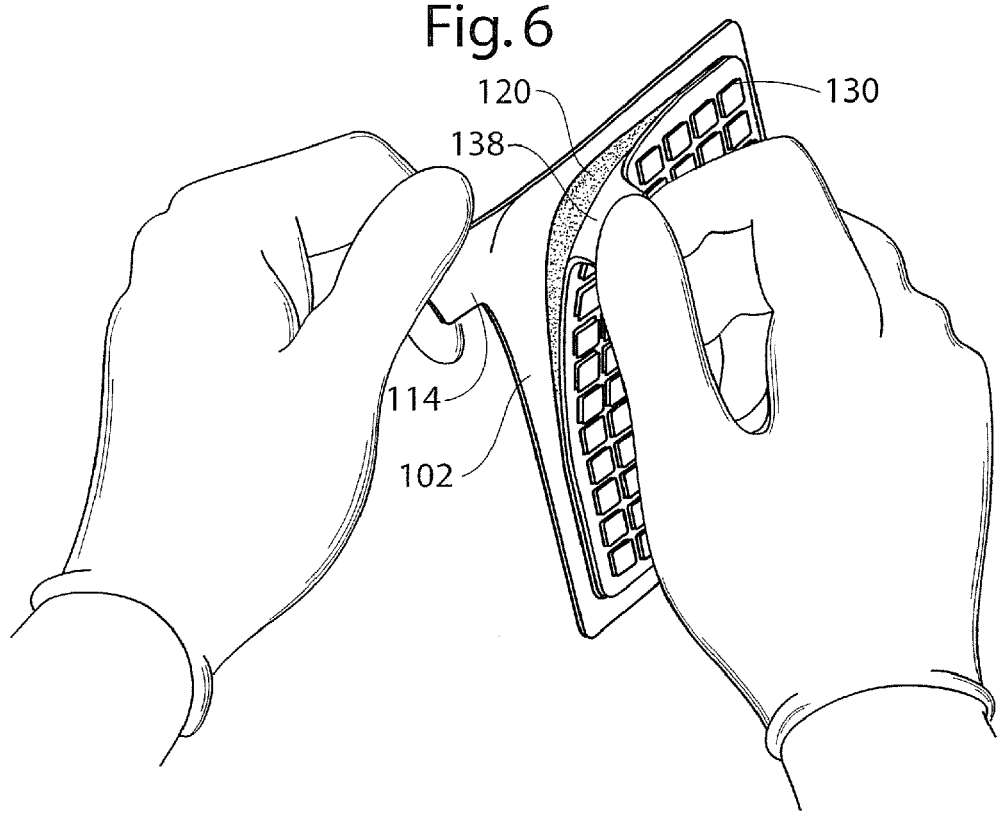
FIGS. 6-15 schematically illustrate an interventional system and/or exemplary operations using the patch assembly of FIG. 3.

The surface of the patient's head 12 is suitably prepared by shaving and cleaning, for example. The release liner 102 is peeled away from the base layer 110 to expose the base adhesive 120 (FIG. 6). The patch 100 is applied to the surface of the head 12 such that the flexible layers 110, 134, 136 conform to the head surface and the patch 100 is adhered to the head surface by the base adhesive 120 (FIG. 7). An incise drape or the like may be pre-applied to the skin surface and the patch 100 in turn applied to the incise drape, in which case the patch 110 may likewise be regarded as being mounted on the surface of the head (albeit indirectly). The patch 100 is applied at a location such that the grid pattern 161 spans the region wherein the operator expects to enter the head 12 with an interventional tool or device.

With the patch 100 adhered to the patient's head 12, the patient is placed within an MRI scanner 20. The MRI scanner scans the head 12 and generates corresponding MR image data. From the MR image data, MR images are obtained of the patient's head that visualize the patient's skull and brain. The MR images also visualize the MRI-visible masses 146 of the patch 100, which serve as MRI-visible landmarks. The MR images can include volumetric high-resolution images of the brain.

Figure 8:
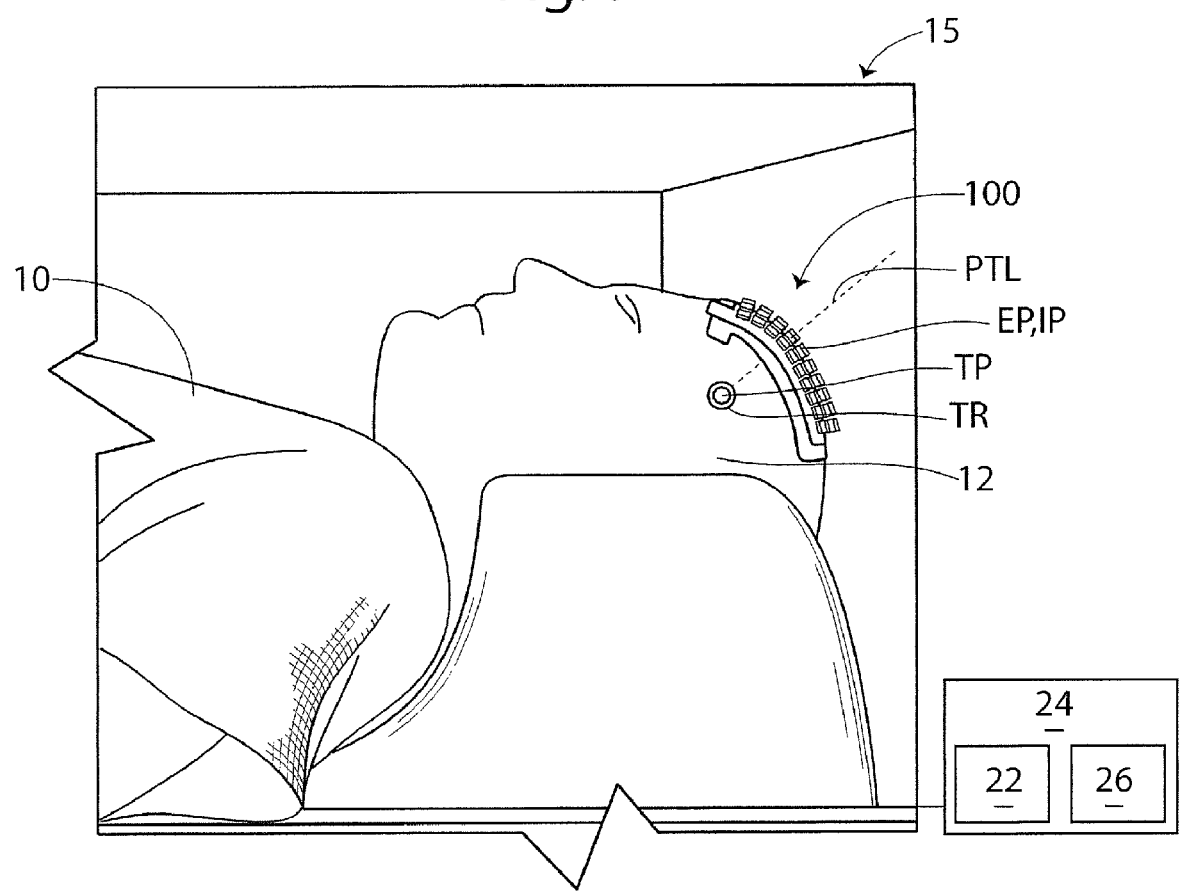

With reference to FIG. 8, a target region TR (which may also be referred to as a region of interest or target therapeutic site) in the head 12 is identified in the MR images. To identify the target region TR, certain known anatomical landmarks can be used. For example, reference may be made to physiological landmarks such as the AC, PC and MCP points (brain atlases give the location of different anatomies in the brain with respect to these points) and other anatomical landmarks of the patient's head.

A target point TP within the target region TR is selected and designated in a logical space in the MR image. A planned trajectory line PTL is selected and designated extending from the target point TP to a desired reference point (such as an operative pivot point of the trajectory guide apparatus 44 discussed hereinbelow). The planned trajectory line PTL extends through an entry surface of the head 12 at a desired entry location point EP in the logical space. According to some embodiments, the pivot point is located at or proximate the entry location point EP. Images are obtained in the planned plane of trajectory to confirm that the trajectory is viable (i.e., that no complications with anatomically sensitive areas should occur). The steps of identifying the target region TR, identifying the target point TP, and/or selecting and designating the planned trajectory line PTL may be executed using or with the aid of the trajectory guide module 24B, for example.

A point of intersection IP between the logical planned trajectory line PTL and the patch 100 in the logical space is determined. More particularly, according to some embodiments, the point of intersection IP between the planned trajectory line PTL and the array 168 of MRI-visible masses 146 is determined.

Figure 9A:
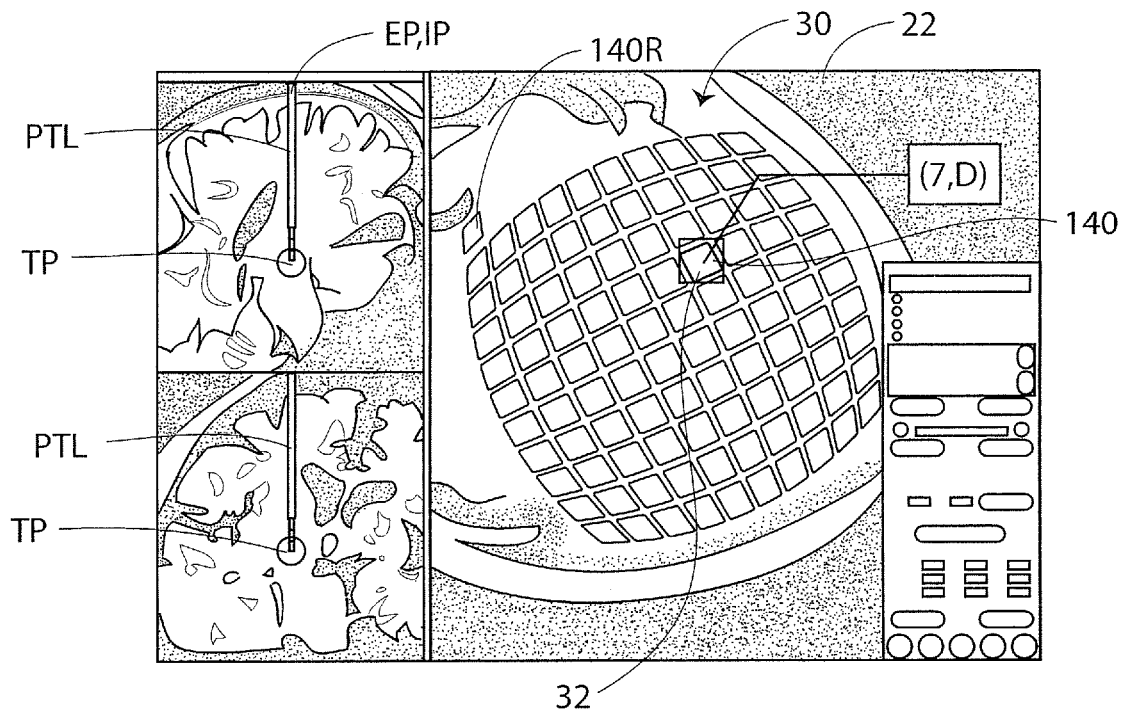

The intersection point IP may be determined by visually displaying the same on the display 22 where it can be readily identified by the operator (for example, as shown in FIG. 9A). For example, a representation or highlight of the planned trajectory line PTL and/or the intersection point IP can be programmatically determined by the controller 24 and overlaid or projected onto an image 30 of the tab array 168. The image 30 may further include the MR image of the patient and/or an overlaid representation of the target point TP. The operator can determine the coordinates of the intersected tab 140 by determining the row number and column number of the tab 140 in the array 168 (FIG. 1), for example.

Alternatively or additionally, the controller 24 may programmatically identify or recognize and analyze and/or report the MRI-visible masses 146 in the image data.

According to some embodiments, the controller 24 (e.g., using the patch recognition module 24A) processes the acquired image data to programmatically recognize, orient and place the patch 100 in the logical space. According to some embodiments, the controller 24 uses an algorithm to programmatically determine the position of the tab array 168 in the logical space. According to some embodiments, the controller uses a pre-stored reference image or images to programmatically determine the position of the tab array 168 in the logical space.

Once the controller 24 has assessed the position (e.g., including orientation) of the patch 100 in the logical space, the controller 24 can use this data to identify the intersection point IP or enable or assist identification of the intersection point IP by the operator. For example, the controller 24 may enhance (e.g., add increased image contrast) or insert highlighted representations of the tabs 140 into the image 30 as provided on the display 22 in order to make the intersected tab 140 and/or the tab array 168 visually stand out in the image 30.

Figure 9B:
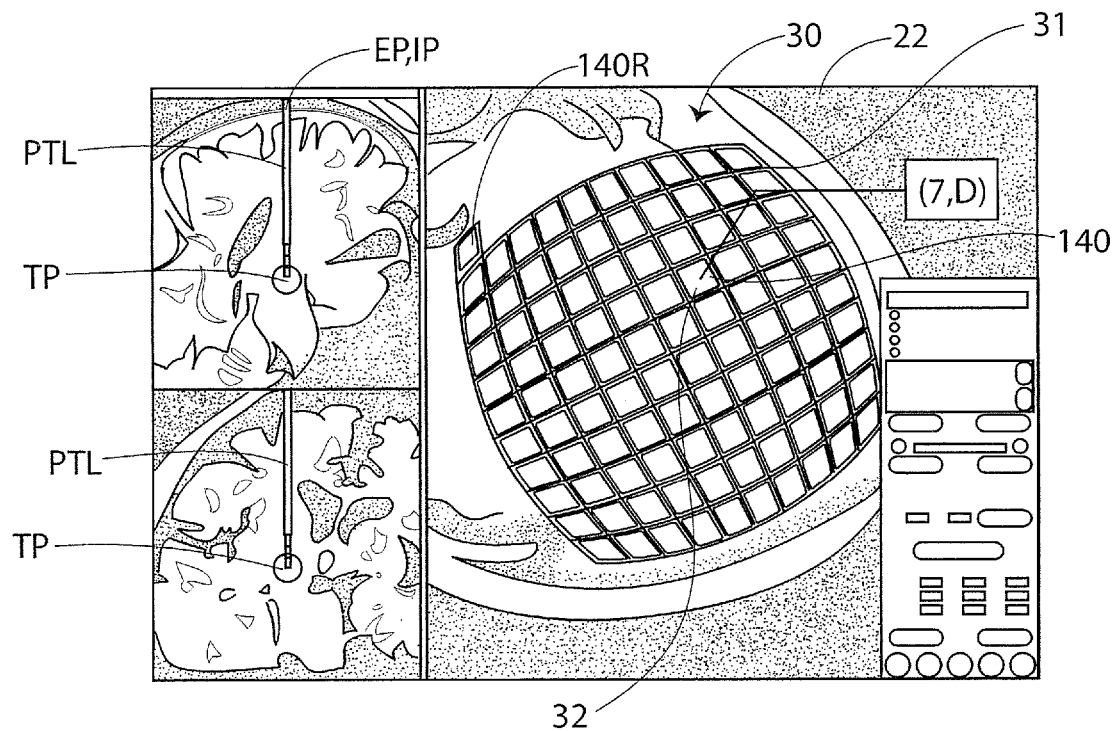

According to some embodiments, the controller 24 generates, fits and overlays or superimposes a graphical grid overlay 31 onto the MR image 30 as shown in FIG. 9B, for example, to delineate the location and distribution of the patch 100 on the head. The positions and orientations of the patch 100 and the MRI-visible tab may be correlated to the image of the head 12 by the graphical grid overlay 31. According to some embodiments, the graphical grid overlay 31 is fitted to the contours of the patch 100 in three dimensional space as illustrated, for example. This may be accomplished by segmenting the image of the tab array 168 and incorporating assessed angle data (of the edges of the tabs 140) in the process of drawing and fitting the graphical grid overlay 31.

The controller 24 may determine and report or indicate the coordinates from the grid 163 corresponding to the intersection point IP to the operator (e.g., visually via the display 22 and/or audibly via a sound transducer). For example, in FIG. 9A, the intersection point IP is located in the MRI-visible tab 140 located in column 5 and row C of the grid 163, and the graphical representation of the intersection point IP is labeled in the image 30 with these coordinates (as illustrated, "(7, D)", designating the tab 140 at column "7" and row "D") and a graphic overlay 32. The operator and/or the controller 24 can also determine the portion or region (e.g., quadrant) of the tab 140 within which the intersection point IP resides.

The reference tab 140R can be identified in the image 30 and used by the operator and/or the controller 24 to determine and register the orientation of the coordinate system 161 of the patch 100 in the logical (i.e., MR volume) frame of reference.

The controller 24 can provide various additional functionality once it has recognized the tab array 168 in the MR image 30. According to some embodiments, the controller 24 will issue an alert (e.g., visible or audible) to the operator if the planned trajectory line PTL does not intersect the grid 163. According to some embodiments, the controller 24 will initially position a provisional planned trajectory line through the center of the grid 163. The operator can then move the provisional planned trajectory line in the display as needed to arrive at the desired ultimate planned trajectory line PTL.

The physical location on the top layer 130 corresponding to the intersection point IP can be readily determined using the image from the MR image data (e.g., by comparison to the image of the tabs 140 in the MR image and/or by reference to the coordinate system 161). Because the top layer 130 is affixed to the head 12 and the relationship between the patient's scalp and the MRI-visible tabs 140 is thereby maintained, the physical location of the intersection point IP (and, thus, the entry location point EP) can likewise be readily identified.

According to some embodiments and as illustrated, the thickness of the patch 100 between the tabs 140 and the underlying surface of the head 12 is thin (e.g., no more than 0.003 and 0.100 inch) so that the intersection point IP between the planned trajectory line PTL and the array 168 is substantially the same or closely proximate the intersection point between the planned trajectory line PTL and the surface of the head 12.

Figure 10:
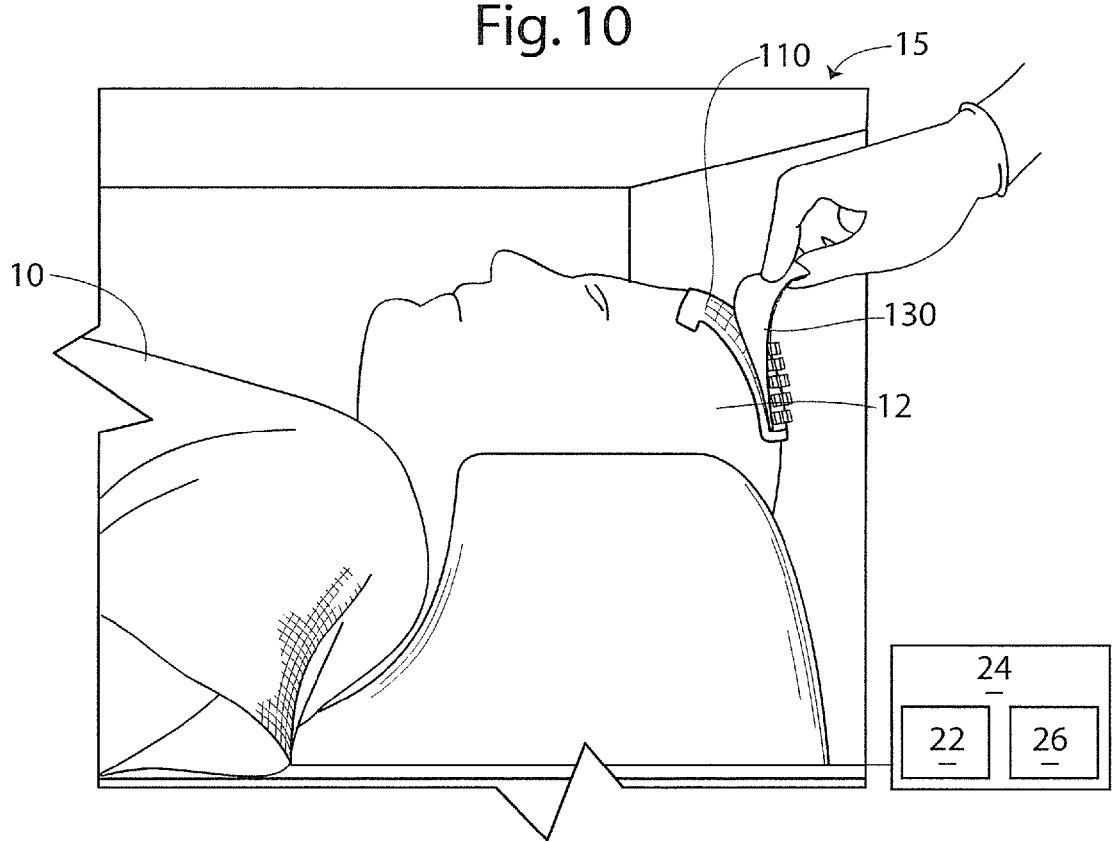

Once the MR image(s) have been acquired for determining the intersection point IP, the patient can be withdrawn from the scanning apparatus 20 to facilitate access to the patient's head 12. The operator removes the top layer 130 from the base layer 110 to reveal the base layer 110 by lifting an edge of the top layer 130 and peeling the top layer 130 away from the base layer 110 as shown in FIG. 10, for example.

With the base layer 110 remaining on the head 12 and exposed, the operator identifies the location (referred to herein as the label point LP) on the base layer 110 corresponding to the location of the intersection point IP in the top layer 130. This identification may be enabled by a prescribed correspondence between the coordinate system 151 of the base layer 110 and the array 168 of MRI-visible tabs 140 (FIG. 5). For example, in the foregoing step, the operator may determine that the intersection point IP was located in the top, right quadrant of the tab 140 located at column "5", row "C" of the array 168. The operator can, in the present step, locate the quadrant located in the top, right quadrant of the square sector 152A (FIG. 5) located at column "5", row "C" of the coordinate system 151 and identify this quadrant as the corresponding label point LP. According to some embodiments, the coordinate system 151 (FIG. 5) is readily legible on the base layer 110 so that the operator can expeditiously and reliably identify the label point LP without special tools or cumbersome procedure.

Having identified the label point LP, the operator may thereafter mark the head 12 at a location on the head surface corresponding to the label point LP. According to some embodiments, the operator marks the head surface at a location immediately below the label point LP. It will be appreciated that this location on the head surface is substantially the same as the intended entry location point EP designated above for the planned trajectory line PTL. The patch 100 thus can provide precise correlation between the logical points in the scanned MR volume and the physical patient.

Figure 11:
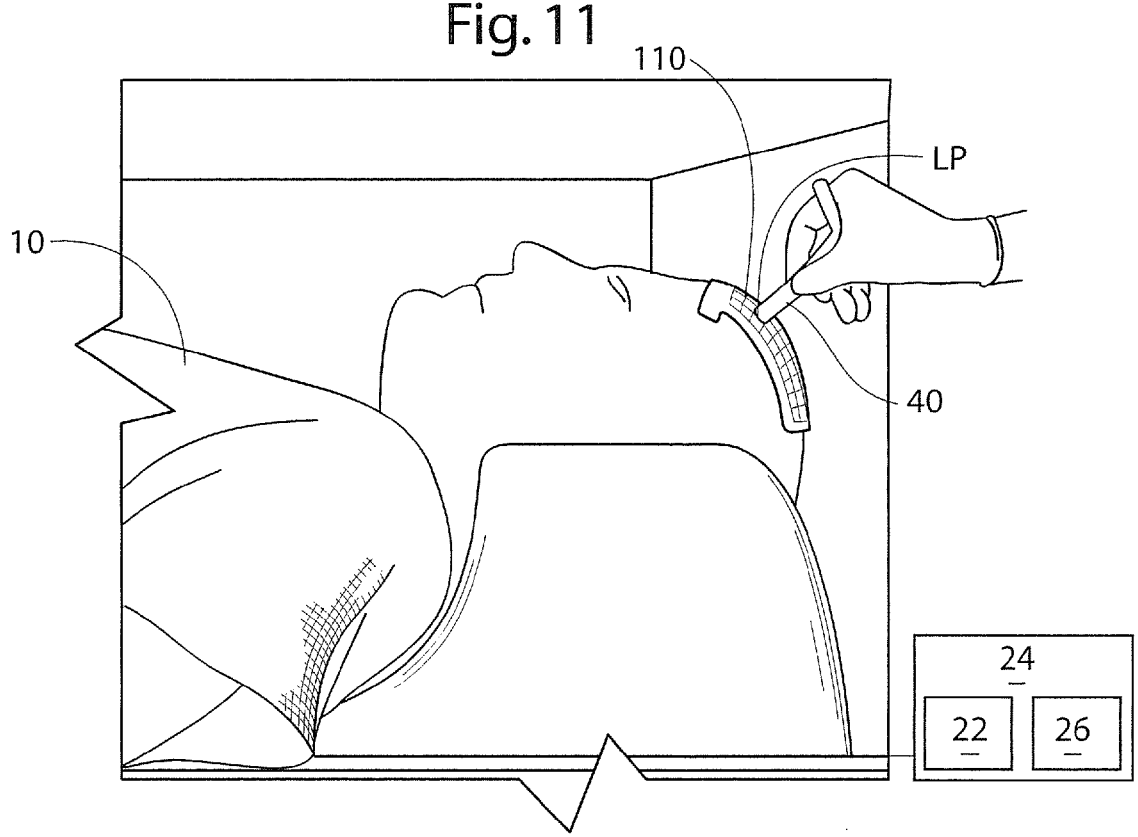

The operator can mark the head 12 at or proximate the desired entry location using a suitable tool or implement. According to some embodiments and as shown in FIG. 11, the operator uses a marking tool 40 in the form of a driver. The operator presses the marking tool 40 into the patient's head 12 such that the marking tool 40 penetrates through the skin and may partially penetrate into the skull. The marking tool 40 may be driven through the base layer 110 and into the head 12. Alternatively, the operator may lift or remove a portion of the base layer 110 to expose the location on the scalp to be marked and then mark the scalp. A visually identifiable mark 14 (FIG. 13) will thereafter remain in the patient's scalp and/or skull for the physician's reference. Suitable marking tools may include marking tools as disclosed in co-assigned U.S. Provisional Patent Application No. 61/041,500, the disclosure of which is incorporated herein by reference. Alternatively, the operator may mark the scalp with ink or other suitable material.

Figure 12:
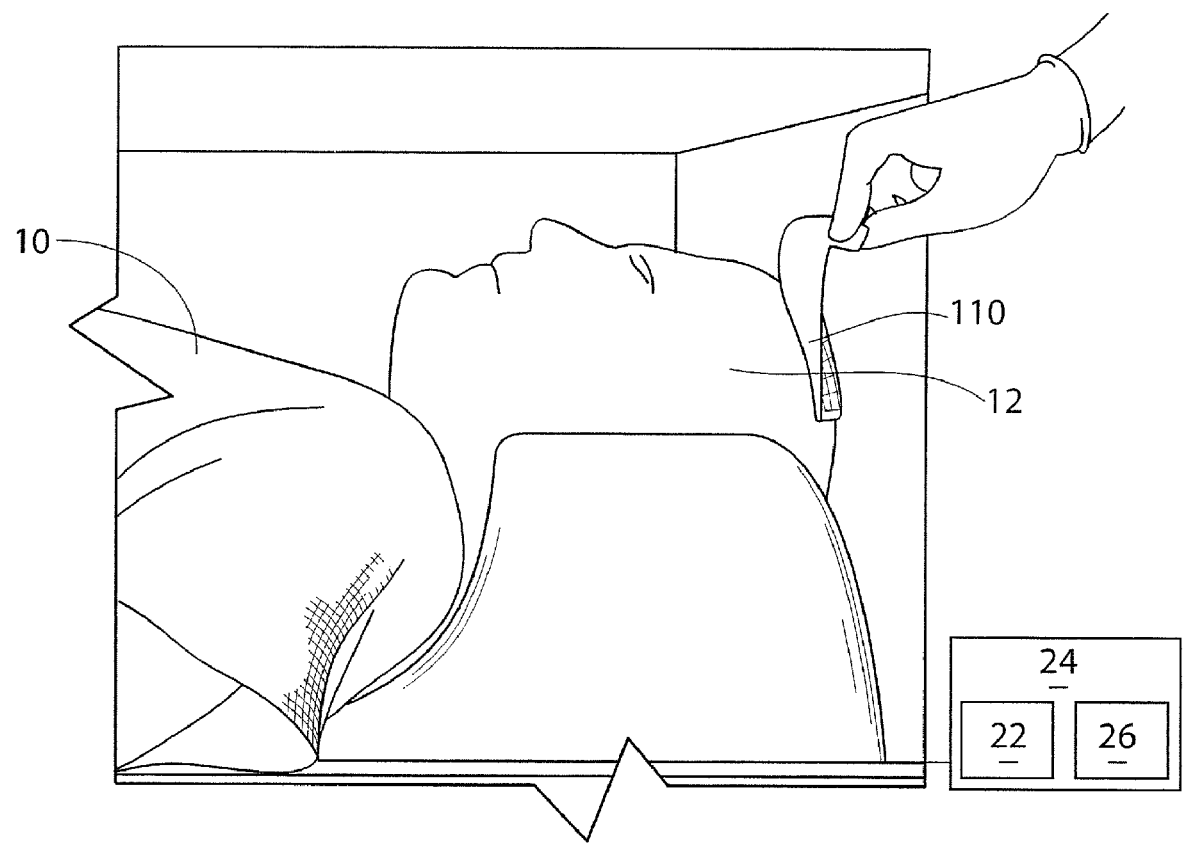
Figure 13:
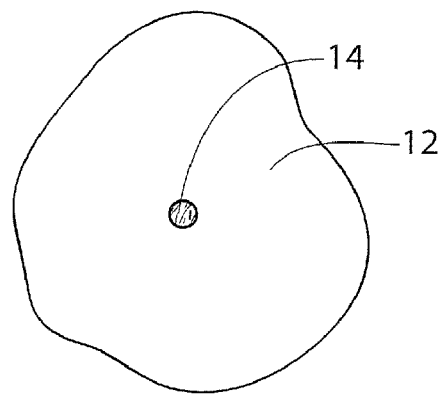
Figure 14:
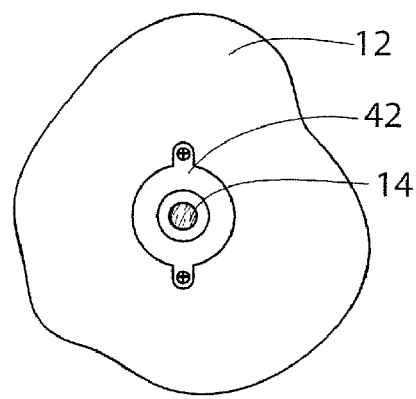

The base layer 110 is removed (e.g., peeled away) from the head 12 as shown in FIG. 12.

A burr hole 16 (FIG. 14) can thereafter be formed in the head 12 at the location of the mark 14 using any suitable technique or device (e.g., drilling). A burr hole ring 42 (FIG. 14) may be affixed to the skull 12 overlying the burr hole 16.

The procedure may thereafter be continued using the burr hole 16 as an access portal to the brain and employing suitable instrumentation such as the trajectory guide apparatus 44. The trajectory guide apparatus 44 can be fixed to the skull of the patient as shown in FIG. 15, for example. The trajectory guide apparatus 44 may allow the operator to align an access path trajectory to the internal target site TP, such that the interventional/surgical device/lead, therapy, etc. will be delivered to the target site following the desired trajectory (e.g., the planned trajectory line PTL) through the cranial tissue. This trajectory goes through the entry location point EP. The interventional device (e.g., probe, lead or the like) can be advanced through a targeting cannula 44B of the trajectory guide apparatus 44, into the head 12 and to or proximate the target point TP. In some embodiments, the trajectory guide apparatus 44 can pivot the targeting cannula 44B about a pivot point at or proximate the entry point location EP. The trajectory guide apparatus 44 may be remotely repositioned using a trajectory guide apparatus controller 44A, for example. Suitable trajectory guide apparatus and methods may include those disclosed in co-assigned PCT Application No. PCT/US2006/045752 and co-assigned U.S. patent application Ser. No. 12/134,412, the disclosures of which are incorporated herein by reference.

In some embodiments, the controller 24 is in communication with a graphical user interface (GUI) that allows a clinician to define a desired trajectory and/or end position on a displayed image, then can electronically convert the orientation/site input data programmatically to generate position data for the trajectory guide apparatus 44. The GUI can include an interactive tool that allows a clinician to draw, trace or otherwise select and/or identify the target treatment site and/or access path trajectory. The system 15 can then be configured to identify adjustments to the trajectory guide apparatus 44 that are most likely to achieve this trajectory.

In some embodiments, the user interface 26 can be configured to electronically determine the location of a targeting cannula and a trajectory associated therewith. The user interface 26 can be configured to display MRI images with the planned trajectory and intersection point(s) that will be followed if the interventional/surgical device/lead is advanced using a defined position of the trajectory guide apparatus 44.

According to some embodiments the patch assembly 101 is packaged as a medical kit with the marking tool 40. The patch assembly 101 may be used in conjunction with a burr hole forming tool (e.g., a drill) configured to drill, cut or otherwise form a burr hole through the patient's skull 12. According to some embodiments, the marking tool 40 and the burr hole forming tool are formed of MRI-compatible materials.

Figure 16:
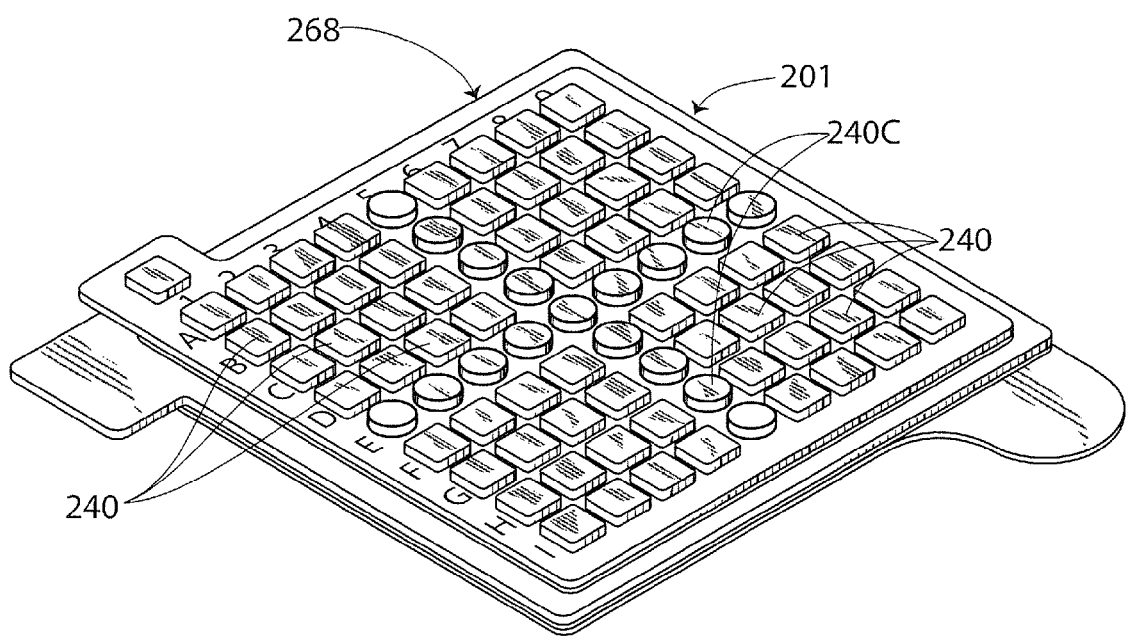
FIG. 16 is a top perspective view of a patch assembly according to further embodiments of the present invention.

With reference to FIG. 16, a patch assembly 201 according to further embodiments of the present invention is shown therein. The patch assembly 201 corresponds to the patch assembly 101 except that the tabs 240C of the center row and the center column of the tab array 268 have a geometric shape (as shown, circular) different than the geometric shape (as shown, rectangular) of the remaining tabs 240. The respective shapes are distinguishable from one another when observed in the MR image. This combination of dissimilar tab shapes may assist the operator or controller 24 in identifying the location of the tab 240 or 240C intersecting the planned trajectory line PTL.

Figure 17:
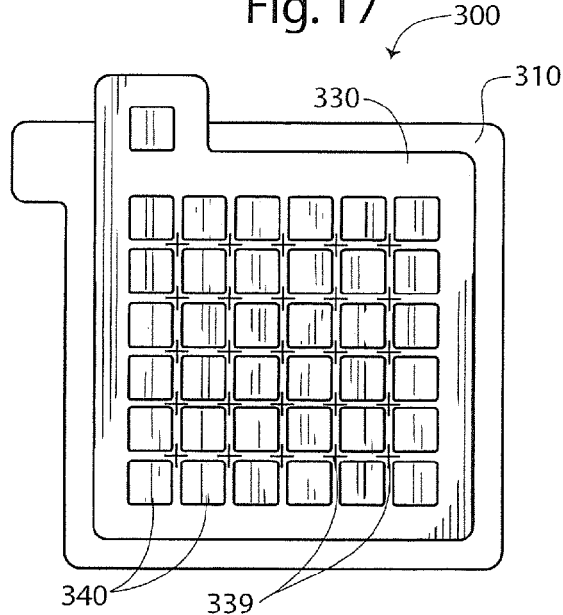
FIG. 17 is a top plan view of a patch according to further embodiments of the present invention.
Figure 18:
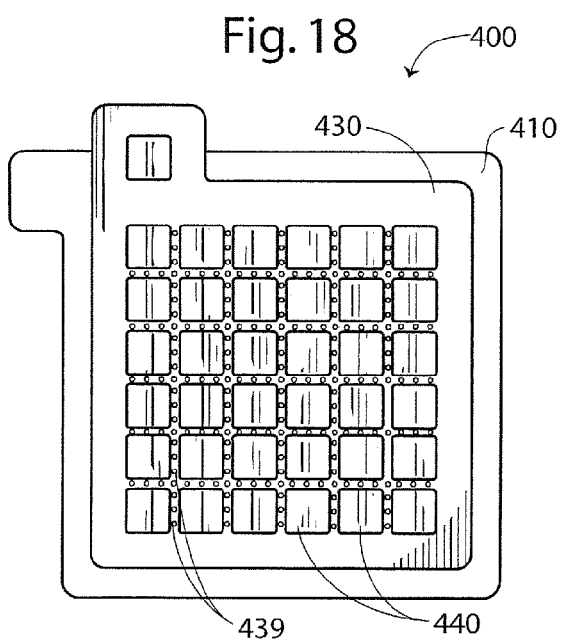
FIG. 18 is a top plan view of a patch according to further embodiments of the present invention.
Figure 19:
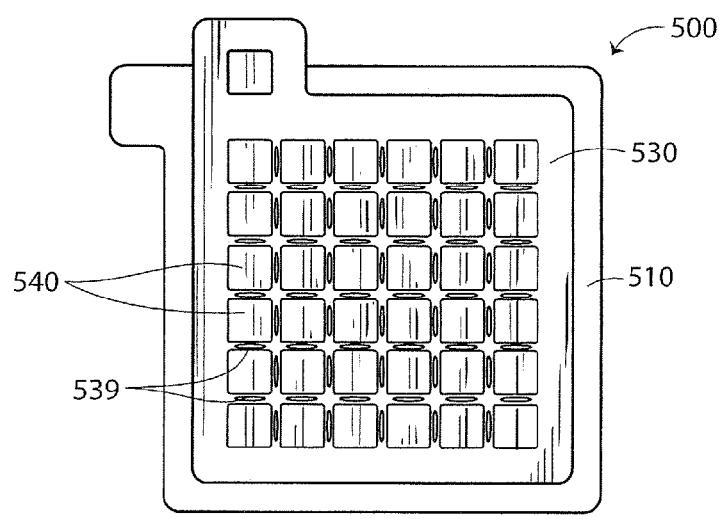
FIG. 19 is a top plan view of a patch according to further embodiments of the present invention.

With reference to FIGS. 17-19, patches 300, 400, 500 according to further embodiments of the present invention are shown therein. The patches 300, 400, 500 each correspond to the patch 100 except that they further include perforations extending through the top layers 330, 430, 530 thereof between the tabs 340, 440, or 540. As illustrated, in some embodiments, the perforations may be configured as closed slits 339, circular holes 439, or open, elongated slots 539. In use, the perforations may help the top layer 330, 430, 530 to conform to the patient's head. The base layers 310, 410, 510 may also include perforations (e.g., extending along the grid lines) to help the base layer 310, 410, 510 conform to the patient's head. According to some embodiments, reliefs that do not extend fully through the top layer 330, 430, 530 may be used in place of the perforations.

Figure 20:
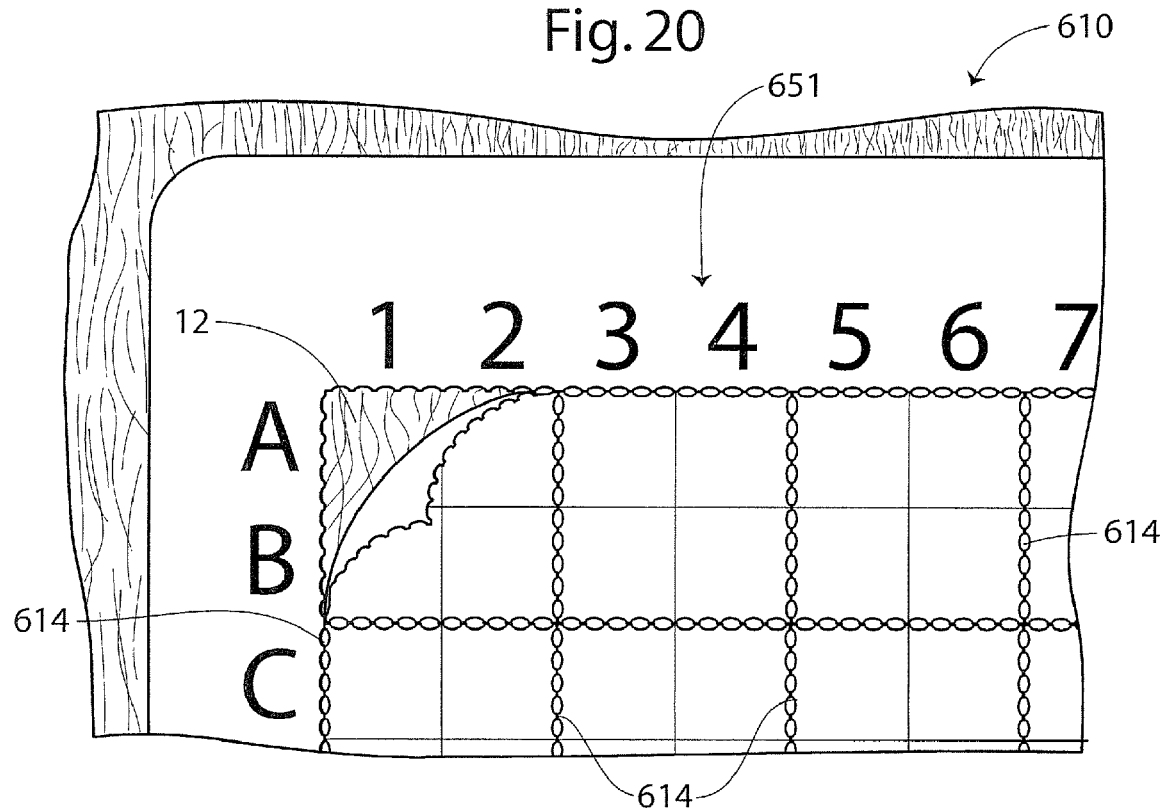
FIG. 20 is a top plan view of a base layer according to further embodiments of the present invention, wherein a portion of the base layer is partially removed.

With reference to FIG. 20, a base layer 610 according to further embodiments of the present invention is shown therein. The base layer 610 may be used in place of the base layer 110 for the patch 100, for example, and corresponds to the base layer 110 except as follows. The base layer 610 can include a grid of perforations 614 generally coextensive with the grid of the base coordinate system 651. The base layer 610 may be used in the same manner as the base layer 110 except that the operator may selectively tear away or remove a section of the base layer 610 along the perforations 614 in order to expose the underlying scalp for marking with the marking tool. According to further embodiments, the base layer 110 may be rendered frangible by score lines or other suitable features.

Figure 21:
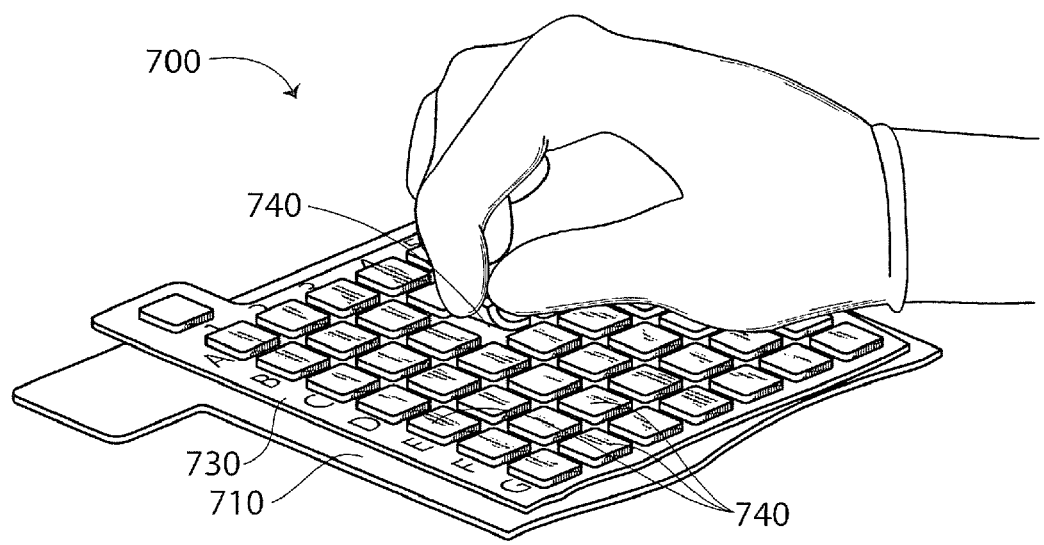
FIG. 21 is a top perspective view of a patch according to further embodiments of the present invention, wherein a tab or component thereof is partially removed.
Figure 22:
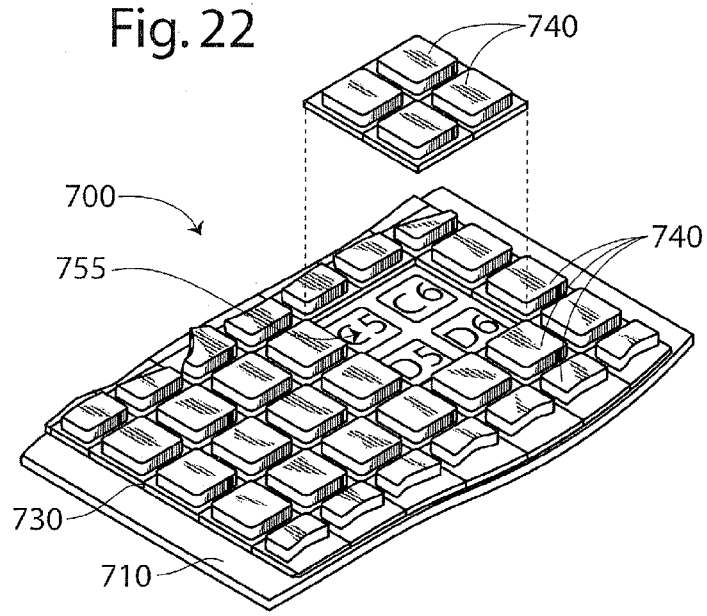
FIG. 22 is a top perspective view of the patch of FIG. 21, wherein a group of tabs thereof is partially removed.

With reference to FIGS. 21 and 22, a patch 700 according to further embodiments of the present invention is shown therein. The patch 700 corresponds to the patch 100 except that the tabs 740 thereof can be removed individually or in subgroups from the remainder or the top layer 730. In use, the operator can remove a selected one or ones of the tabs 740 from the patient's head to reveal the underlying base layer 710. The base layer 710 may also be frangible (e.g., including perforations corresponding to the perforations 614), in which case the underlying segment of the base layer 710 may also be selectively removed to expose the patient's scalp for marking. Indicia 755 may be visible on the base layer 710 where the tabs 740 have been removed.

Figure 23:
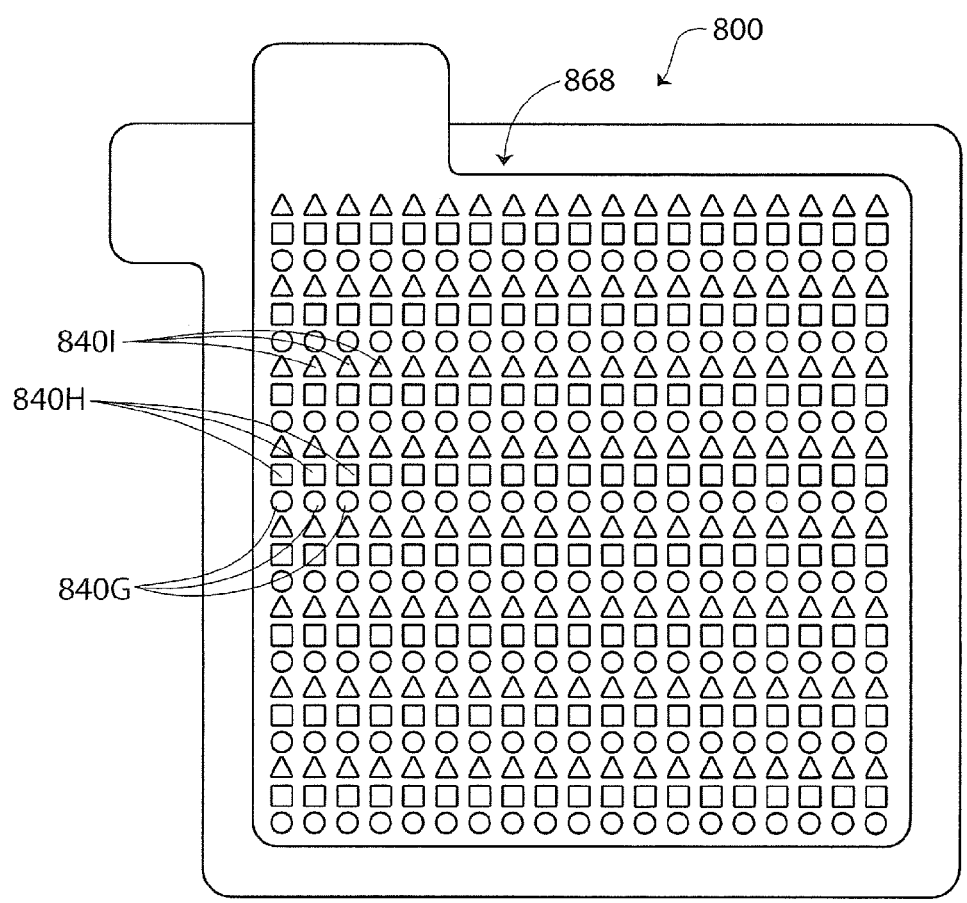
FIG. 23 is a plan view of a patch according to further embodiments of the present invention.

With reference to FIG. 23, a patch 800 according to further embodiments of the present invention is shown therein. The patch 800 may correspond to the patch 100 except that the tab array 868 of the patch 800 includes rows of MRI-visible tabs 840G, 840H, 840I having distinctly different geometric shapes (as shown, a circular shape, a square shape, and a triangular shape, respectively). The different tab shapes are discernable from an MR image of the patch 800 by an operator and/or the controller 24. The configuration of the tab array 868 may facilitate determination of the orientation of the patch 100 in logical space and/or identification of the tab 840G, 840H, 840I intersected by the planned trajectory line PTL.

Figure 24:
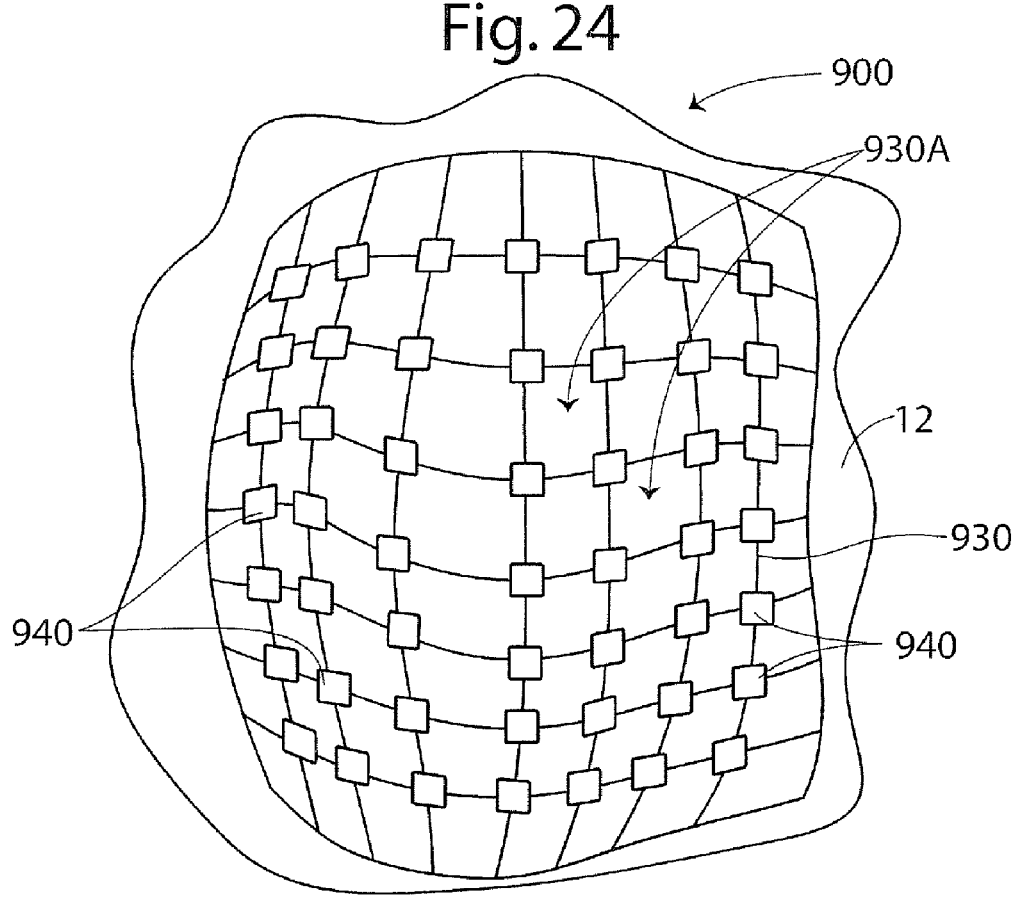
FIG. 24 is a plan view of a patch according to further embodiments of the present invention mounted on a patient's head.

With reference to FIG. 24, a patch 900 according to further embodiments of the present invention is shown therein. The patch 900 may correspond to the patch 100 except that the patch 900 includes a mesh ("fishnet") substrate 930 to which an array 968 of MRI-visible tabs 940 (corresponding to the tabs 140) are secured. The substrate 930 can be elastic or stretchable to readily deform or conform to the contours of a head 12. The patch 900 may be used in the same manner as the patch 100 except that in some embodiments the patch 900 may not include any base layer corresponding to the base layer 110. In this case, the operator may identify and mark the desired location (e.g., the point of intersection IP) through the openings 930A of the mesh substrate 930 and the mesh substrate 930 may be adhered directly to the head (or an incise drape) by adhesive on the back surface of the mesh substrate 930. The controller 24 may recognize and assess the tab array 968 and construct a modified grid in logical space that corresponds to the distorted or irregular distribution of the tabs 940 caused by the stretching of substrate 930. The controller 24 may recognize and assess the tab array 968 and construct a modified grid in logical space that corresponds to the distorted or irregular distribution of the tabs 940 caused by the stretching of the substrate 930. According to still further embodiments, the layers 110 and 130 of the patch 100 may be stretchable (with or without being meshes) to enable similar stretchable conformability to the head 12.

Figure 25:
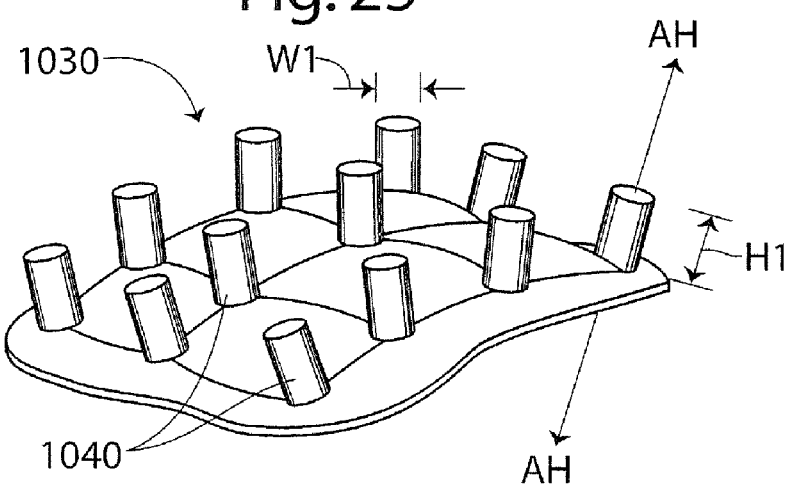
FIG. 25 is a fragmentary, perspective view of a top layer including MRI-visible tabs according to further embodiments of the present invention.

With reference to FIG. 25, a top layer 1030 according to further embodiments of the present invention is shown therein. The top layer 1030 may be used in place of the top layer 130, for example. The top layer 1030 differs from the top layer 130 in that the top layer 1030 includes MRI-visible tabs 1040 each having a height dimension H1 greater than its width W1. The height of each tab 1040 is sufficient to permit the controller 24 and/or an operator to determine the orientation of a heightwise axis AH-AH of the tab 1040. This additional information can be employed to more accurately assess the point of intersection IP with the planned trajectory line PTL.

Figure 26:
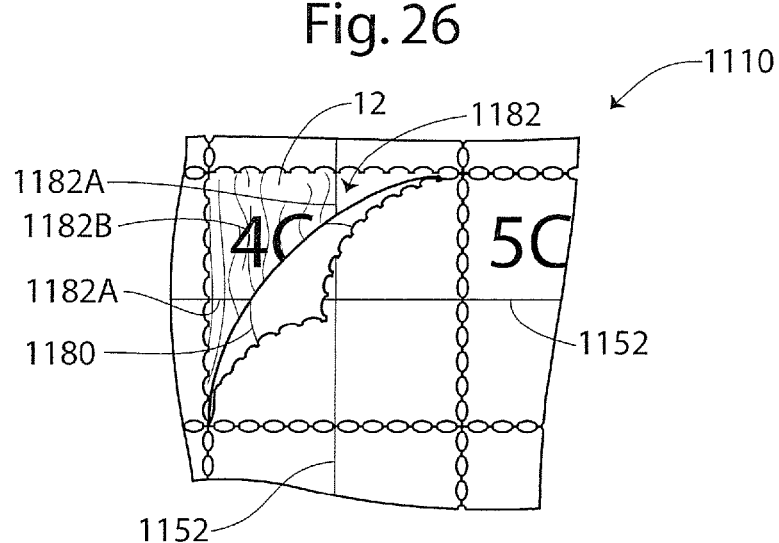
FIG. 26 is a fragmentary, plan view of a base layer according to further embodiments of the present invention mounted on a patient's head and wherein a portion of the base layer is partially removed.

With reference to FIG. 26, a base layer 1110 according to further embodiments of the present invention is shown therein. The base layer 1110 may be used in place of the base layer 110 or the base layer 610, for example. The base layer 1110 differs from the base layer 610 in that the base layer 1110 includes a supply of ink 1180 therein and/or thereon. When the base layer 1110 is applied to the head 12, the ink 1180 transfers to the head 12 to leave an ink pattern 1182 on the surface of the head. For example, the ink pattern 1182 can include a full or partial duplicate 1182A of the grid lines 1152 on the base layer 1110 and/or textual or codified indicia 1182B indicating the coordinates. The base layer 1110 can be used in the same manner as the base layer 110 or the base layer 610 except that the base layer 1110 can be fully or partially removed prior to marking the head 12 with a marking tool or the like. In this case, the ink pattern 1182 remains on the scalp to assist the operator in marking the physical location corresponding to the intersection point IP determined from the MR image 30.

The ink 1180 may be any suitable material that can transfer from the base layer 1110 to the patient's scalp, bond or adhere to the scalp, and provide a suitably visible contrast with the scalp. The ink may be a liquid or powder, for example.

According to further embodiments, the ink supply may be provided in or on the substrate including the MRI-visible tabs (e.g., the top layer 130) in which case the base layer (e.g., the base layer 110) can be omitted. The substrate can be removed after the MRI scan is taken, leaving the ink pattern on the scalp of the head 12 to provide the reference grid on the head 12 for locating the physical location of the intersection point IP.

Figure 27:
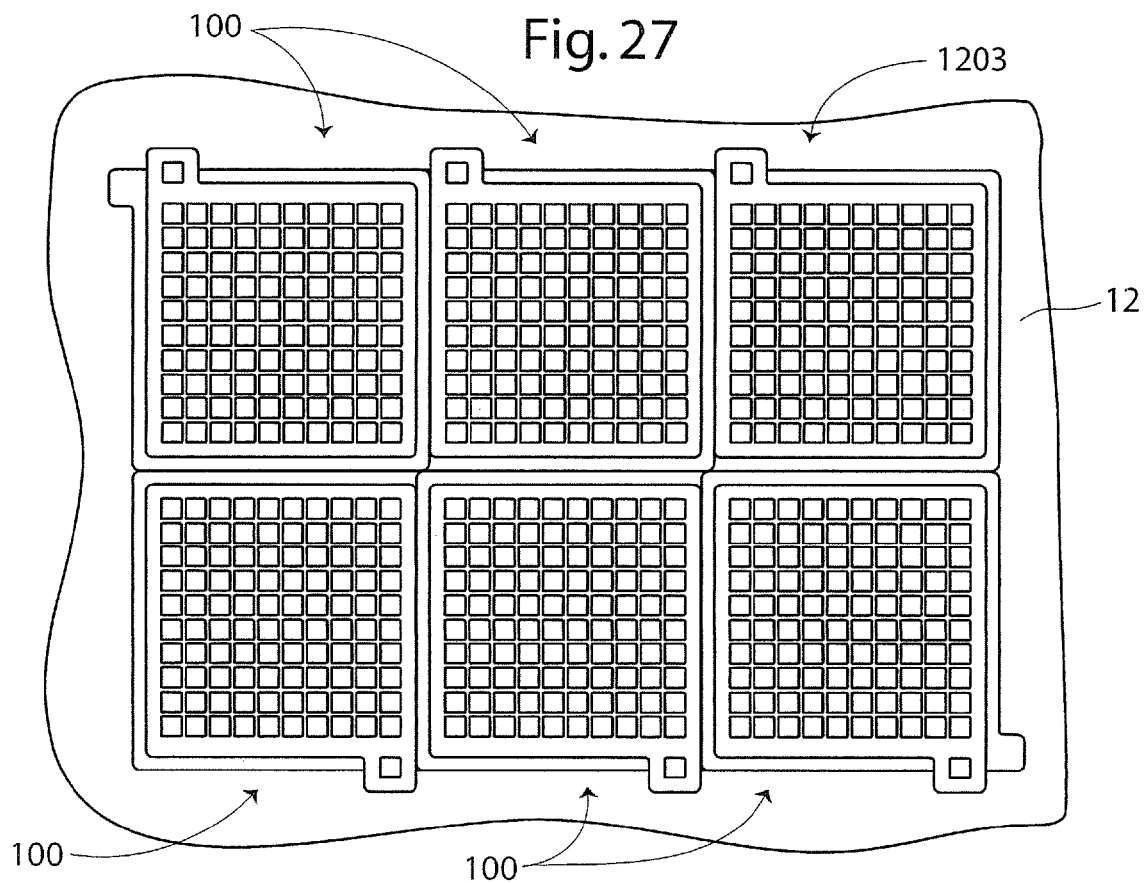
FIG. 27 is a plan view of a patch system according to embodiments of the present invention mounted on a patient.

With reference to FIG. 27, a patch system 1203 and method according to further embodiments of the present invention are illustrated therein. The patch system 1203 includes a plurality of the patches 100, for example, applied to the patient 12 in close proximity to one another to form a patch array 1208. The patches 100 may be tiled together (i.e., placed in close proximity to one another) and may or may not be immediately adjacent one another or overlapping. The patch system 1203 may be used in generally the same manner as the patch 100 as described above, except that the patch system 1203 will cover a greater surface area on the patient and only one of the patches 100 thereof will be intersected by the planned trajectory line PTL. The operator may visually determine which of the patches contains the intersection point IP and where the intersection point IP lies in the patch. According to some embodiments, the controller 24 programmatically assesses the patch system 1203 in the MR image to determine and indicate, report or otherwise process the positions of the patches 100 as discussed above with regard to the patch 100. The controller 24 may correlate the plurality of patches 100 with respect to one another so that the patch system 1203 can be assessed and processed in substantially the same manner as the single patch 100. The controller 24 may programmatically account for variations resulting from relative placements of the patches 100 in the patch array 1208. According to some embodiments, the controller 24 determines the orientation of each patch 100 using each patch's respective reference tab 140R as described above.

Still further embodiments of the present invention may incorporate aspects or features as described herein in other forms, combinations and/or applications. For example, a flexible substrate having selectively removable MRI-visible tabs (such as the substrate 730 and the tabs 740) may be provided without a base layer (e.g., the base layer 710) and may be directly applied to a patient's body surface or incise drape.

By way of further example, a patch may be provided having a base layer (e.g., corresponding to the base layer 110) and a removable top layer (e.g., corresponding to the top layer 130), but wherein the top layer carries only a single (i.e., exactly one) MRI-visible fiducial element or tab. The single MRI-visible fiducial element may have an asymmetric shape that is discernable in an MRI image so that the orientation of the patch in the logical space can be determined from the MRI image data. According to some method embodiments, the orientation of a patch (with or without a base layer) having only a single MRI-visible fiducial element is programmatically determined (e.g., by the controller 24) from the MRI image data. According to still further embodiments, the patch (with our without a base layer) may have a plurality of MRI-visible fiducial elements, but wherein the fiducial elements are not arranged in a defined pattern.

Two patches (or groups of patches) in accordance with the present invention (e.g. two of the patches 100) can be employed together to identify and mark two entry location points for a bilateral surgical procedure on a patient's head. The two patches 100 may be concurrently mounted on the head and each patch used in the same manner as discussed above. In this case, the controller 24 may programmatically distinguish between the two patches and their respective planned trajectory lines PTL so that the point of intersection IP for each patch can be determined independently of the other. The controller 24 may simultaneously display the patches 100 and their associated points of intersection IP, planned trajectory lines PTL, graphical overlays and the like.

Figure 28:
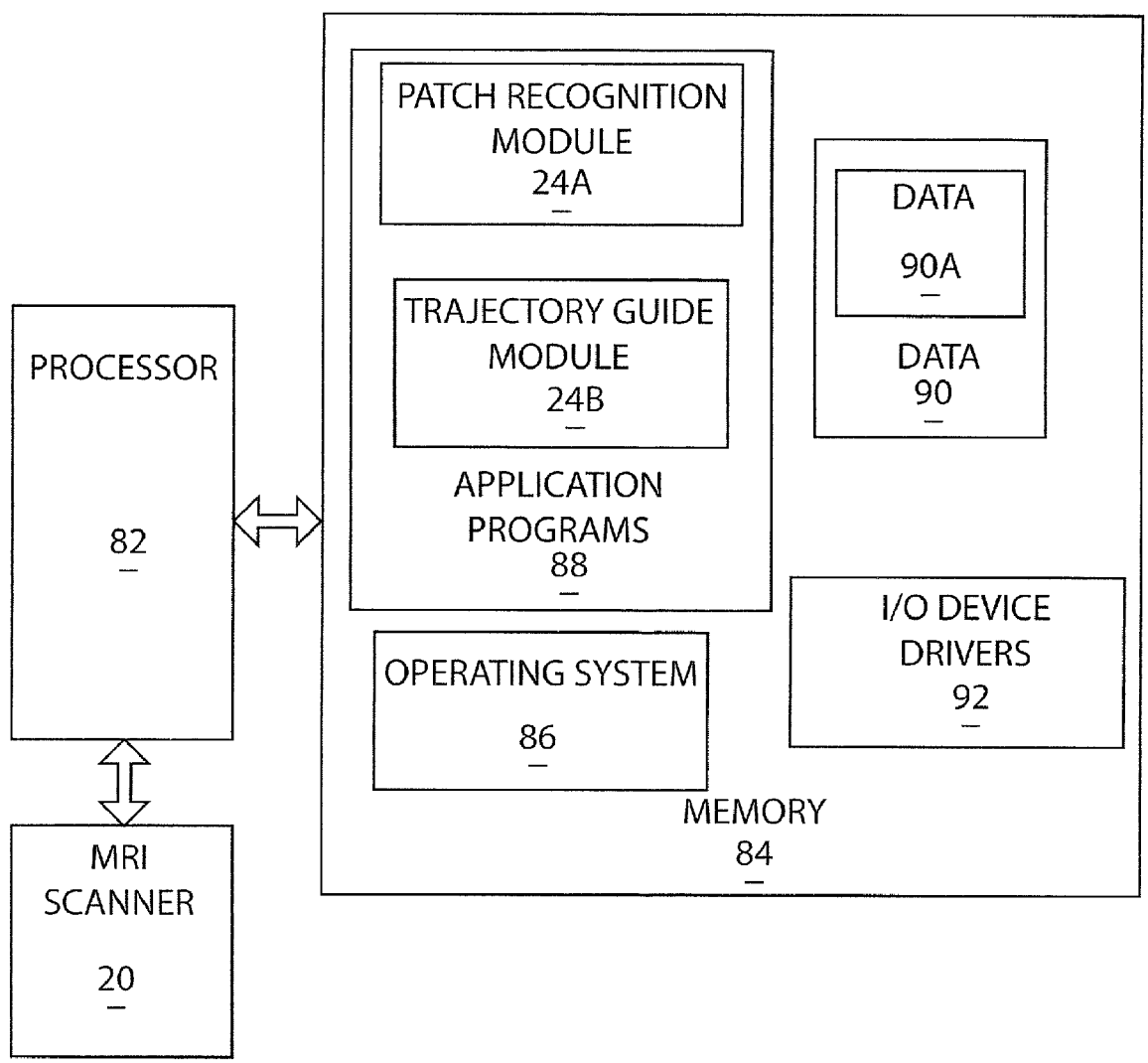
FIG. 28 is a data processing system according to embodiments of the present invention.

The system 15 (FIG. 7) can include circuits or modules that can comprise computer program code used to automatically or semi-automatically carry out operations to generate multi-dimensional visualizations during an MRI guided therapy. FIG. 28 is a schematic illustration of a circuit or data processing system 80 that can be used with the system 15. The circuits and/or data processing systems 80 data processing systems may be incorporated in a digital signal processor in any suitable device or devices. As shown in FIG. 28, the processor 82 communicates with an MRI scanner 20 and with memory 84 via an address/data bus 85. The processor 82 can be any commercially available or custom microprocessor. The memory 84 is representative of the overall hierarchy of memory devices containing the software and data used to implement the functionality of the data processing system.

The memory 84 can include, but is not limited to, the following types of devices: cache, ROM, PROM, EPROM, EEPROM, flash memory, SRAM, and DRAM.

As shown in FIG. 28 illustrates that the memory 84 may include several categories of software and data used in the data processing system: the operating system 86; the application programs 88; the input/output (I/O) device drivers 92; and data 90. The data 90 can also include tool and patient-specific image data 90A. FIG. 28 also illustrates the application programs 88 can include the patch recognition module 24A and the trajectory guide module 24B.

As will be appreciated by those of skill in the art, the operating systems 452 may be any operating system suitable for use with a data processing system, such as OS/2, AIX, DOS, OS/390 or System390 from International Business Machines Corporation, Armonk, N.Y., Windows CE, Windows NT, Windows95, Windows98, Windows2000 or other Windows versions from Microsoft Corporation, Redmond, Wash., Unix or Linux or FreeBSD, Palm OS from Palm, Inc., Mac OS from Apple Computer, LabView, or proprietary operating systems. The I/O device drivers 92 typically include software routines accessed through the operating system 86 by the application programs 88 to communicate with devices such as I/O data port(s), data storage 90 and certain memory 84 components. The application programs 88 are illustrative of the programs that implement the various features of the data processing system and can include at least one application, which supports operations according to embodiments of the present invention. Finally, the data 90 represents the static and dynamic data used by the application programs 88, the operating system 86, the I/O device drivers 92, and other software programs that may reside in the memory 84.

While the present invention is illustrated, for example, with reference to the modules 24A-24B being application programs in FIG. 28, as will be appreciated by those of skill in the art, other configurations may also be utilized while still benefiting from the teachings of the present invention. For example, the modules 24A, 24B and/or may also be incorporated into the operating system 86, the I/O device drivers 92 or other such logical division of the data processing system. Thus, the present invention should not be construed as limited to the configuration of FIG. 28 which is intended to encompass any configuration capable of carrying out the operations described herein. Further, one or more of modules, i.e., modules 24A, 24B can communicate with or be incorporated totally or partially in other components, such as an MRI scanner.

The I/O data port can be used to transfer information between the data processing system, the MRI scanner, the tool and another computer system or a network (e.g., the Internet) or to other devices controlled by the processor. These components may be conventional components such as those used in many conventional data processing systems, which may be configured in accordance with the present invention to operate as described herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. An MRI-compatible patch for identifying a location, the patch comprising:
   a flexible base layer that is mountable on and substantially conformable to a patient's body surface, the base layer having opposed upper and lower primary surfaces;
   a flexible substrate that is releasably attached to the upper primary surface of the base layer and substantially conformable to the patient's body surface;
   a plurality of MRI-visible fiducial elements defined by or secured to the flexible substrate, wherein the MRI-visible fiducial elements are arranged in a defined pattern; and
   indicia on the base layer corresponding to the MRI-visible fiducial elements on the flexible substrate, wherein the indicia has a second prescribed pattern having a higher resolution than the defined pattern of the MRI-visible fiducial elements on the flexible substrate.

2. The patch of claim 1 including a layer of adhesive disposed on a lower surface of the flexible substrate and engaging the upper primary surface of the base layer and releasably attaching the flexible substrate to the base layer.

3. The patch of claim 1 including an adhesive disposed on the lower primary surface of the base layer to attach the base layer to the body surface.

4. The patch of claim 3 including a release liner releasably backing the adhesive on the lower primary surface of the base layer.

5. The patch of Claim 1 including second indicia on the flexible substrate corresponding to the indicia on the base layer.

6. The patch of Claim 1 wherein the defined pattern includes a grid pattern defining a coordinate system.

7. The patch of claim 6 including codified indicia representing the coordinate system.

8. The patch of claim 6 wherein the MRI-visible fiducial elements are discrete elements arranged in a defined grid of columns and rows of the MRI-visible fiducial elements.

9. The patch of claim 1 wherein the flexible substrate includes a pull tab to facilitate removal of the flexible substrate from the base layer.

10. The patch of claim 1 wherein the base layer is frangible to permit selective access to the body surface when the base layer is mounted thereon and the flexible substrate has been at least partially removed.

11. The patch of claim 1 including at least one MRI-visible reference indicator to indicate an orientation of the patch.

12. The patch of Claim 1 wherein at least one of the MRI-visible fiducial elements has a first MRI-visible geometric shape, and at least one of the MRI-visible fiducial elements has a second MRI-visible geometric shape different from the first MRI-visible geometric shape.

13. The patch of Claim 1 wherein at least some of the MRI-visible fiducial elements include a pocket containing MRI-visible material.

14. The patch of claim 13 wherein the MRI-visible material includes an MRI-visible liquid.

15. The patch of Claim 1 wherein at least some of the MRI-visible fiducial elements are selectively discretely removable from the flexible substrate.

16. The patch of claim 1 including perforations defined in the flexible substrate to thereby enhance conformity of the flexible substrate to the body surface.

17. The patch of claim 1 wherein the flexible substrate is formed of a stretchable material to allow the flexible substrate to conform to a head body surface.

18. The patch of claim 1 wherein the flexible substrate is a mesh.

19. The patch of claim 1 including a supply of ink that is transferable to the patient's body surface when the patch is mounted on the patient's body surface.

20. The patch of claim 1 wherein at least one of the MRI-visible fiducial elements has a width and a height greater than its width to define a heightwise axis.

21. The patch of claim 1 wherein the flexible substrate has a thickness in the range of from about 0.001 to 0.100 inches.

22. The patch of claim 1 wherein the flexible substrate is a substrate material selected from the group consisting of polyvinyl, PET, silicone, polyethylene, polyurethane, and polyamide.

23. The patch of claim 1 further including:
    an adhesive disposed on the lower primary surface of the base layer adapted to attach the base layer to the body surface;
    a release liner releasably secured to the adhesive on the lower primary surface of the base layer; and
    at least one MRI-visible reference indicator to indicate an orientation of the patch;
    wherein at least some of the MRI-visible fiducial elements include a pocket containing MRI-visible liquid; and
    wherein the defined pattern includes a grid pattern defining a coordinate system.

24. The patch of claim 23 wherein:
    the patch includes a layer of adhesive disposed on a lower surface of the flexible substrate and engaging the upper primary surface of the base layer and releasably attaching the flexible substrate to the base layer;
    the indicia represents the coordinate system;
    the base layer and the flexible substrate are adapted to be substantially conformable to a head body surface of the patient;
    the flexible substrate has a thickness in the range of from about 0.001 to 0.100 inches; and
    the flexible substrate is a substrate material selected from the group consisting of polyvinyl, PET, silicone, polyethylene, polyurethane, and polyamide.

25. The patch of claim 1 wherein the flexible substrate includes a flexible sheet and the MRI-visible fiducial elements are releasably secured to the flexible sheet.

26. The patch of claim 25 including a layer of adhesive disposed on a lower surface of the flexible sheet and engaging the upper primary surface of the base layer and releasably attaching the flexible sheet to the base layer.

27. The patch of claim 25 wherein the flexible sheet is peelably releasably attached to the base layer such that the flexible sheet can be peeled off of the base layer with the MRI-visible fiducial elements disposed on the flexible sheet.

28. A medical kit for designating a physical location on a head of a patient, the medical kit comprising:
    a patch including:
    a flexible base layer that is mountable on and substantially conformable to a patient's body surface, the base layer having opposed upper and lower primary surfaces;
    a flexible substrate that is releasably attached to the upper primary surface of the base layer and substantially conformable to the patient's body surface;
    a plurality of MRI-visible fiducial elements defined by or secured to the flexible substrate, wherein the MRI-visible fiducial elements are arranged in a defined pattern; and
    indicia on the base layer corresponding to the MRI-visible fiducial elements on the flexible substrate, wherein the indicia has a second prescribed pattern having a higher resolution than the defined pattern of the MRI-visible fiducial elements on the flexible substrate; and
a head marking tool being configured to mark the head of the patient.

29. The medical kit of claim 28 wherein the head marking tool is configured to mark a skull of the patient.

* * * * *